US009311789B1

(12) United States Patent
Gwin

(10) Patent No.: US 9,311,789 B1
(45) Date of Patent: Apr. 12, 2016

(54) SYSTEMS AND METHODS FOR SENSORIMOTOR REHABILITATION

(71) Applicant: BIOSENSICS LLC, Cambridge, MA (US)

(72) Inventor: Joseph T. Gwin, Boston, MA (US)

(73) Assignee: BIOSENSICS LLC, Cambridge, MA (US)

( * ) Notice: Subject to any disclaimer, the term of this patent is extended or adjusted under 35 U.S.C. 154(b) by 19 days.

(21) Appl. No.: 14/248,956

(22) Filed: Apr. 9, 2014

Related U.S. Application Data

(60) Provisional application No. 61/810,141, filed on Apr. 9, 2013.

(51) Int. Cl.
*G08B 23/00* (2006.01)
*G08B 1/08* (2006.01)
*G05B 1/01* (2006.01)
*G08C 19/00* (2006.01)

(52) U.S. Cl.
CPC .. *G08B 1/08* (2013.01); *G05B 1/01* (2013.01); *G08C 19/00* (2013.01)

(58) Field of Classification Search
CPC ...... A61B 5/11; A61B 5/1116; A61B 5/1124; A61B 5/4519; A61B 5/4528; A61B 5/486; A61F 4/00; A61F 5/0102; A61H 1/0237; A61H 1/0274; A61H 1/0281; A61H 2201/5007; A61H 2201/5064; B25J 9/0006
USPC ................ 340/573.1, 539.1, 539.12, 539.23, 340/539.24, 539.25, 648, 691.6, 5.52, 5.53, 340/5.61, 5.64, 7.51
See application file for complete search history.

(56) References Cited

U.S. PATENT DOCUMENTS

| | | | |
|---|---|---|---|
| 3,702,999 A | 11/1972 | Gradisar | |
| 5,373,651 A | 12/1994 | Wood | |
| 5,396,227 A | 3/1995 | Carroll et al. | |
| 5,642,096 A | 6/1997 | Leyerer et al. | |
| 5,697,791 A | 12/1997 | Nashner et al. | |
| 5,907,819 A | 5/1999 | Johnson | |
| 6,119,516 A * | 9/2000 | Hock | 73/379.01 |
| 6,201,476 B1 | 3/2001 | Depeursinge et al. | |
| 6,433,690 B2 | 8/2002 | Petelenz et al. | |
| 6,730,024 B2 | 5/2004 | Freyre et al. | |

(Continued)

FOREIGN PATENT DOCUMENTS

| | | |
|---|---|---|
| EP | 1195139 A1 | 4/2002 |
| WO | WO 03/065891 A2 | 8/2003 |

OTHER PUBLICATIONS

U.S. Appl. No. 13/723,040, filed Dec. 20, 2012, Najafi et al., Unpublished.

(Continued)

*Primary Examiner* — Daniel Previl
(74) *Attorney, Agent, or Firm* — Knobbe, Martens, Olson & Bear, LLP

(57) ABSTRACT

A sensorimotor rehabilitation system can analyze body movement kinematics of a person, and in particular analyze the use of limbs (e.g., upper limbs) to provide feedback for sensorimotor rehabilitation. Parameters of body movement (e.g., quantity and type of body movement) can be assessed based on data recorded from an inertial sensor affixed or connected to, for example, an upper limb of a person or outer clothing such as a sleeve. Automated feedback can be provided to the user to improve sensorimotor rehabilitation.

25 Claims, 8 Drawing Sheets

(56) References Cited

U.S. PATENT DOCUMENTS

| | | | |
|---|---|---|---|
| 6,890,285 B2 | 5/2005 | Rahman et al. | |
| 6,895,341 B2 | 5/2005 | Barrey et al. | |
| 6,926,667 B2 | 8/2005 | Khouri | |
| 6,997,882 B1 | 2/2006 | Parker et al. | |
| 7,141,026 B2* | 11/2006 | Aminian et al. | 600/595 |
| 7,166,063 B2 | 1/2007 | Rahman et al. | |
| 7,334,472 B2 | 2/2008 | Seo et al. | |
| 7,450,730 B2 | 11/2008 | Berg et al. | |
| 7,620,450 B2 | 11/2009 | Kim et al. | |
| 7,627,450 B2 | 12/2009 | Lee et al. | |
| 7,632,216 B2 | 12/2009 | Rahman et al. | |
| 7,634,379 B2 | 12/2009 | Noble | |
| 7,640,134 B2 | 12/2009 | Park et al. | |
| 7,701,354 B2 | 4/2010 | Chung | |
| 7,725,289 B2 | 5/2010 | Nagashima et al. | |
| 7,747,409 B2 | 6/2010 | Ladetto et al. | |
| 7,771,371 B2 | 8/2010 | Avni | |
| 7,857,771 B2 | 12/2010 | Alwan et al. | |
| 7,890,291 B2 | 2/2011 | Godin et al. | |
| 7,962,308 B2 | 6/2011 | Makino | |
| 7,983,872 B2 | 7/2011 | Makino et al. | |
| 8,007,450 B2 | 8/2011 | Williams | |
| 8,025,632 B2 | 9/2011 | Einarsson | |
| 8,109,890 B2 | 2/2012 | Kamiar et al. | |
| 8,206,325 B1 | 6/2012 | Najafi et al. | |
| 8,212,650 B2 | 7/2012 | Tsern et al. | |
| 8,242,879 B2 | 8/2012 | Haynes et al. | |
| 8,287,477 B1 | 10/2012 | Herr et al. | |
| 8,376,971 B1 | 2/2013 | Herr et al. | |
| 8,384,551 B2 | 2/2013 | Ross et al. | |
| 8,388,553 B2 | 3/2013 | James et al. | |
| 8,551,029 B1 | 10/2013 | Herr et al. | |
| 8,657,772 B2 | 2/2014 | Einarsson | |
| 8,753,275 B2 | 6/2014 | Najafi et al. | |
| 8,979,665 B1 | 3/2015 | Najafi et al. | |
| 9,005,141 B1 | 4/2015 | Najafi et al. | |
| 2003/0065409 A1 | 4/2003 | Raeth et al. | |
| 2003/0078528 A1 | 4/2003 | Rahman et al. | |
| 2003/0139692 A1 | 7/2003 | Barrey et al. | |
| 2004/0015103 A1 | 1/2004 | Aminian et al. | |
| 2005/0043660 A1 | 2/2005 | Stark et al. | |
| 2005/0165336 A1 | 7/2005 | Rahman et al. | |
| 2006/0140425 A1 | 6/2006 | Berg et al. | |
| 2006/0166157 A1 | 7/2006 | Rahman et al. | |
| 2006/0270949 A1 | 11/2006 | Mathie et al. | |
| 2007/0060445 A1* | 3/2007 | Reinkensmeyer et al. | 482/1 |
| 2007/0149359 A1 | 6/2007 | Rahman et al. | |
| 2007/0270214 A1 | 11/2007 | Bentley | |
| 2007/0293781 A1 | 12/2007 | Sims et al. | |
| 2008/0091762 A1 | 4/2008 | Neuhauser et al. | |
| 2008/0281555 A1 | 11/2008 | Godin et al. | |
| 2008/0281636 A1 | 11/2008 | Jung et al. | |
| 2008/0318683 A1 | 12/2008 | Rofougaran et al. | |
| 2009/0002152 A1 | 1/2009 | Chung | |
| 2009/0024065 A1 | 1/2009 | Einarsson | |
| 2009/0055223 A1 | 2/2009 | Jung et al. | |
| 2009/0058660 A1 | 3/2009 | Torch | |
| 2009/0069724 A1 | 3/2009 | Otto et al. | |
| 2009/0076345 A1 | 3/2009 | Manicka et al. | |
| 2009/0099495 A1 | 4/2009 | Campos et al. | |
| 2009/0192414 A1 | 7/2009 | Yasuhara | |
| 2009/0195350 A1 | 8/2009 | Tsern et al. | |
| 2009/0234249 A1 | 9/2009 | Randolph | |
| 2009/0292194 A1 | 11/2009 | Libbus et al. | |
| 2009/0293319 A1 | 12/2009 | Avni | |
| 2010/0121227 A1 | 5/2010 | Stirling et al. | |
| 2010/0286571 A1 | 11/2010 | Allum et al. | |
| 2010/0324455 A1 | 12/2010 | Rangel et al. | |
| 2011/0054359 A1 | 3/2011 | Sazonov et al. | |
| 2011/0071443 A1* | 3/2011 | Weisz et al. | 601/40 |
| 2011/0115629 A1 | 5/2011 | Holler et al. | |
| 2011/0136626 A1* | 6/2011 | Wei et al. | 482/6 |
| 2011/0246123 A1* | 10/2011 | DelloStritto et al. | 702/141 |
| 2011/0300994 A1* | 12/2011 | Verkaaik et al. | 482/51 |
| 2012/0022667 A1 | 1/2012 | Accinni et al. | |
| 2013/0059696 A1* | 3/2013 | Hijmans et al. | 482/8 |
| 2013/0245785 A1 | 9/2013 | Accini et al. | |

OTHER PUBLICATIONS

American Diabetes Association, Apr. 7-8, 1999, Boston, Massachusetts, "Consensus development conference in diabetic foot wound care", Diabetes Care 22.8:1354 (Aug. 1999).

Altini, M., et al., "A low-power multi-modal body sensor network with application to epileptic seizure monitoring", Conf Proc IEEE Eng Med Biol Soc, p. 1806-9 (2011).

Aminian et al., "Spatio-temporal parameters of gait measured by an ambulatory system using miniature gyroscopes," *Journal of Biomechanics*, vol. 35:689-699 (2002).

Aminian et al., "Temporal feature estimation during walking using miniature accelerometers: an analysis of gait improvement after hip arthroplasty," *Medical & Biological Engineering & Computing*, vol. 37:686-691 (1999).

Anderson, C. "Private payers look to telemedicine", Healthcare IT News, 2013.

U.S. Appl. No. 14/219,935, filed Mar. 19, 2014, Najafi et al., Unpublished.

Armstrong et al., "Activity patterns of patients with diabetic foot ulceration", Diabetes Care, vol. 26(9):2595-2597 (2003).

Armstrong et al., "Continuous activity monitoring in persons a high risk for diabetes-related lower-extremity amputation", Journal of the American Podiatric Medical Association, vol. 91:451-455 (2001).

Armstrong et al., "Evaluation of removable and irremovable cast walkers in the healing of diabetic foot wounds: a randomized controlled trial", Diabetes Care, vol. 28:551-4 (2005).

Armstrong et al., "Variability in activity may precede diabetic foot ulceration", Diabetes Care, vol. 27(8):3028-3029 (2004).

Blaivas et al., "A Prospective Comparison of Supine Chest Radiography and Bedside Ultrasound for the Diagnosis of Traumatic Pneumothorax," Acad Emerg Med Sep. 2005, vol. 12, No. 9, pp. 844-849.

Bohannon et al., "Walking speed: reference values and correlates for older adults," *J Orthop Sports Phys Ther*, vol. 24:86-90 (1996).

Bonato, P., "Wearable sensors and systems. From enabling technology to clinical applications", IEEE Eng Med Biol Mag, p. 25-36 (2010).

Brand, Paul W. "The diabetic foot", Diabetes Mellitus, Theory and Practice, 3rd Ed., Ellenberg M. Rifkin H., Ed. New York: Medical Examination Publishing, 1983, pp. 803-828.

Bravata, D.M., et al., "Using Pedometers to Increase Physical Activity and Improve Health: A Systematic Review", Journal of the American Medical Association 298(19):2296-2304 (2007).

Breiman, L., "Random Forests", Machine Learning 45:5-32 (2001).

Brooks, R. "Emergency ultrasound in the acute assessment of haemothorax," Emerg. Med. J. 2004 21: 44-46.

Brown, E. "The year ahead for the ATA, telemedicine", Healthcare IT News, 2013.

Chumbler, N.R., et al., "Effects of telerehabilitation on physical function and disability for stroke patients: a randomized, controlled trial", Stroke, 43(8):2168-74 (2012).

Coleman et al., "The total contact cast, a therapy for plantar ulceration on insensitive feet", J.Am. Podiatr. Med. Assoc., vol. 74:548-552 (1984).

Cummings et al., "Forgetting falls. The limited accuracy of recall of falls in the elderly," *J Am Geriatr Soc*, vol. 36:613-6 (1988).

Dalton, A., et al., "Development of a body sensor network to detect motor patterns of epileptic seizures", IEEE Trans Biomed Eng, 59(11):3204-11 (2012).

Della Toffola, L., et al., "Development of a platform to combine sensor networks and home robots to improve fall detection in the home environment", Conf Proc IEEE Eng. Med. Biol. Soc., p. 5331-4 (2011).

Doughty et al., "The design of a practical and reliable fall detector for community and institutional telecare," *J Telemed Telecare*, vol. 6 Suppl 1:S150-4 (2000).

(56) References Cited

OTHER PUBLICATIONS

Fielding, R.T., "REST: Architectural Styles and the Design of Network-based Software Architectures" University of California, Irvine (2000).
Forducey, P.G., et al., "Telehealth for persons with severe functional disabilities and their caregivers: facilitating self-care management in the home setting", Psychol Serv, 9(2):144-62 (2012).
Go, A.S., et al., "Heart disease and stroke statistics—2013 update: a report from the American Heart Association", Circulation, 127(1):e6-e245 (2013).
Godwin, K.M. et al., "Cost associated with stroke: outpatient rehabilitative services and medication", Top Stroke Rehabil, 18 Suppl 1:676-84 (2011).
Greenwald, R.M., et al., "Head impact severity measures for evaluating mild traumatic brain injury risk exposure", Neurosurgery, 62(4):789-98 (2008); discussion 798 (2008).
Gwin, J.T., et al., "In-situ Measures of Head Impact Acceleration in NCAA Division I Men's Ice Hockey: Implications for ASTM F1045 and Other Ice Hockey Helmet Standards", Journal of ASTM International, 6(6)(2009).
Haaland, K.Y., et al., "Relationship between arm usage and instrumental activities of daily living after unilateral stroke", Arch Phys Med Rehabil, 93(11):1957-62 (2012).
Hailey, D. et al., "Systematic review of evidence for the benefits of telemedicine", J. Telemed Telecare, 8 Suppl 1:1-30 (2002).
Heidenreich, P.A., et al., "Forecasting the future of cardiovascular disease in the United States: a policy statement from the American Heart Association", Circulation, 123(8):933-44 (2011).
Helm et al., "Total contact casting in diabetic patients with neuropathic foot ulcerations", Arch. Phys. Med. Rehabil., vol. 65:691-693 (1984).
Huang et al., "Bound for Success: A Systematic Review of Constraint-Induced Movement Therapy in Children With Cerebral Palsy Supports Improved Arm and Hand Use", dowloaded from http://ptjournal.apta.org/ on Mar. 29, 2014.
Lavery et al., "Reducing dynamic foot pressures in high-risk diabetic subjects with foot ulcerations", Diabetes Care, vol. 19(8):818-821 (1996).
Lindemann et al., "Evaluation of a fall detector based on accelerometers: a pilot study," Med Biol Eng Comput, vol. 43:548-51 (2005).
Mancinelli, C., et al., "Assessing the feasibility of classifying toe-walking severity in children with cerebral palsy using a sensorized shoe", Conf Proc IEEE Eng. Med. Biol. Soc. p. 5163-6 (2009).
Marcus, B.H., et al., "Efficacy of an individualized, motivationally-tailored physical activity intervention", Ann Behav. Med., 20(3):174-80 (1998).
Mateer et al., "Prospective Analysis of Rapid Trauma Ultrasound Examination Performed by Emergency Physicians," The Journal of Trauma: Injury, Infection, and Critical Care, vol. 38(6), Jun. 1995, pp. 879-885.
Mathie et al., "Detection of daily physical activities using a triaxial accelerometer," Medical & Biological Engineering & Computing, 2003, vol. 41, pp. 296-301.
Mizell, "Using gravity to estimate accelerometer orientation", Proceedings of the Seventh IEEE International Symposium on Wearable Computers, Computer Society (2003).
Najafi et al., "Ambulatory system for human motion analysis using a kinematic sensor: Monitoring of daily physical activity in the elderly," Ieee Transactions on Biomedical Engineering, vol. 50:711-723 (2003).
Najafi et al., "Assessing Postural Control and Postural Control Strategy in Diabetes Patients Using Innovative and Wearable Technology", Jour. Diab. Science and Tech. vol. 4(4):780-791 (2010).
Najafi et al., "Measurement of standsit and sit-stand transitions using a miniature gyroscope and its application in fall risk evaluation in the elderly," Ieee Transactions on Biomedical Engineering, vol. 49:843-851 (2002).
Najafi et al., "A novel ambulatory device for continuous 24-H monitoring of physical activity in daily life", North American Congress on Biomechanics (NACOB), Michigan, 2008.

Najafi, B. et al., "Importance of time spent standing for those at risk of diabetic foot ulceration", Diabetes Care, (11):2448-50 (2010).
Noury et al., "A smart sensor based on rules and its evaluation in daily routines," presented at 25th Annual International Conference of the IEEE Eng. Med. Biol. Society (2003).
Oliver et al., "Development and evaluation of evidence based risk assessment tool (STRATIFY) to predict which elderly inpatients will fall: case-control and cohort studies," Bmj, vol. 315:1049-53 (1997).
Page, S.J., et al., "Efficacy of modified constraint-induced movement therapy in chronic stroke: a single-blinded randomized controlled trial", Arch. Phys. Med. Rehabil., 85(1):14-8 (2004).
Page, S.J., et al., "Modified constraint induced therapy: a randomized feasibility and efficacy study", J. Rehabil. Res. Dev., 38(5):583-90 (2001).
Patel, S., et al., "A review of wearable sensors and systems with application in rehabilitation" J. Neuroeng. Rehabil. 9:21 (2012).
Patel, S., et al., "Home monitoring of patients with Parkinson's disease via wearable technology and a web-based application", Conf. Proc. IEEE Eng. Med. Biol. Soc. 2010:4411-4 (2010).
Patel, S., et al., "Longitudinal monitoring of patients with Parkinson's disease via wearable sensor technology in the home setting", Conf. Proc. IEEE Eng. Med. Biol. Soc., 2011:1552-5 (2011).
Patel, S., et al., "Monitoring motor fluctuations in patients with Parkinson's disease using wearable sensors", IEEE Trans. Inf. Technol. Biomed., 13(6):864-73 (2009).
Patel, S., et al., "Tracking motor recovery in stroke survivors undergoing rehabilitation using wearable technology", Conf. Proc. IEEE Eng. Med. Biol. Soc., 2010:6858-61 (2010).
Patel, S., et al., "Using wearable sensors to predict the severity of symptoms and motor complications in late stage Parkinson's Disease", Conf. Proc. IEEE Eng. Med. Biol. Soc., p. 3686-9 (2008).
Pecoraro et al., "Pathways to diabetic limb amputation", Diabetes Care, vol. 13(5):513-521 (1990).
Quinn et al., "What is the utility of the Focused Assessment with Sonography in Trauma (FAST) exam in penetrating torso trauma?" Injury, Int. J. Care Injured 42 (2011) 482-487.
Robnik-Sikonja, M. et al., "Theoretical and empirical analysis of ReliefF and RReliefF", Machine Learning Journal 53:23-69 (2003).
Roger, V.L., et al., "Heart disease and stroke statistics—2012 update: a report from the American Heart Association", Circulation, 125(1):e2-e220 (2012).
Shrirang Mare, D.K., "Is Bluetooth the right technology for mHealth?", in USENIX Workshop on Health Security (HealthSec) 2010.
Sinacore et al., "Diabetic plantar ulcers treated by total contact casting", Phys. Ther. vol. 67:1543-1547 (1987).
Tinetti et al., "Fall risk index for elderly patients based on number of chronic disabilities," Am J Med, vol. 80: 429-34 (1986).
Uswatte, G., et al., "Reliability and validity of the upper-extremity Motor Activity Log-14 for measuring real-world arm use", Stroke, 36(11):2493-6 (2005).
Uswatte, G., et al., "The Motor Activity Log-28: assessing daily use of the hemiparetic arm after stroke", Neurology, 67(7):1189-94 (2006).
Viana, R. et al., "Barriers to the implementation of constraint-induced movement therapy into practice", Top Stroke Rehabil., 19(2):104-14 (2012).
Vipul Goyal, O.P. et al, "Attribute-Based Encryption for Fine-Grained Access Control of Encrypted Data", in ACM CCS2006.
Walker et al., "Chronic diabetic neuropathic foot ulcerations and total contact casting: healing effectiveness and outcome predictability", Arch. Phys. Med. Rehabil., vol. 66:574 (1985).
Wolf, S.L., et al., "Effect of constraint-induced movement therapy on upper extremity function 3 to 9 months after stroke: the EXCITE randomized clinical trial", JAMA, 296(17):2095-104 (2006).
Wolf, S.L., et al., "Pilot normative database for the Wolf Motor Function Test", Arch. Phys. Med. Rehabil., 87(3):443-5 (2006).
Wolf, S.L., et al., "Repetitive task practice: a critical review of constraint-induced movement therapy in stroke", Neurologist, 8(6):325-38 (2002).
Wu et al., "The pivotal role of offloading in the management of neuropathic foot ulceration", Curr. Diab. Rep. vol. 5:423-9 (2005).

(56) References Cited

OTHER PUBLICATIONS

Wu et al., "Use of pressure offloading devices in diabetic foot ulcers", Diabetes Care, vol. 31(11):2118-2119, (2008).

Wu, C.Y., et al., "A randomized controlled trial of modified constraint-induced movement therapy for elderly stroke survivors: changes in motor impairment, daily functioning, and quality of life", Arch. Phys. Med. Rehabil., 88(3):273-8 (2007).

ASTM Standard E2369, 05e1. "Standard Specification for Continuity of Care Record (CCR)", Available from: http://www.astm.org/Standards/E2369.htm, document available on or before Dec. 10, 2008 (per Internet Archive Wayback Machine, http://web.archive.org/web/20081210023950/http://www.astm.org/Standards/E2369.htm), Accessed on Jul. 6, 2015.

Billings, G. "Michigan Becomes 15th State to Pass Private Payer Telehealth Reimbursement. Center for Telehealth and e-Health Law", 2012; Available from: http://ctel.org/2012/07/michigan-becomes-15th-state-to-pass-private-payer-telehealth-reimbursement/.

Chen et al., "Automatic Fall Detection and Risk of Falling Assessment with Wearable Sensors", in Wireless Health, San Diego, CA (2012).

Chen et al., "PAMSys: Long-term physical activity monitoring with single wearable motion sensor", in $2^{nd}$ Conference on Wireless Health (2011).

Chen, B.R., et al., "A web-based system for home monitoring of patients with Parkinson's disease using wearable sensors", IEEE Trans Biomed Eng, 58(3):831-6 (2011).

Cohen, R.S., "The Narrowing Distribution Funnel: How to Get Your Medical Device to Market", Medical Device & Diagnostic Industry Magazine, 1999.

Damodaran, A., Damodaran Online. Available from: http://pages.stern.nyu.edu/~adamodar/pc/datasets/uValuedata.xls, document available on or before Jun. 17, 2011 (per Internet Archive Wayback Machine), Accessed on Jul. 6, 2015.

Del Din, S., et al., "Estimating Fugl-Meyer clinical scores in stroke survivors using wearable sensors", Conf Proc IEEE Eng Med Biol Soc, p. 5839-42 (2011).

Hester, T., et al., "Identification of tasks performed by stroke patients using a mobility assistive device", Conf Proc IEEE Eng. Med. Biol. Soc., 1:1501-4 (2006).

HL7 and ASTM International. HL7/ASTM, Product Brief—Continuity of Care Document (CCD). Available from: http://wiki.hl7.org/index.php?title=Product_CCD, document available on or before Aug. 23, 2011 (per Internet Archive Wayback Machine, http://web.archive.org/web/20110823125253/http://wiki.hl7.org/index.php?title=Product_CCD), Accessed on Jun. 19, 2015.

Mancinelli, C., et al., "A novel sensorized shoe system to classify gait severity in children with cerebral palsy", Conf Proc IEEE Eng. Med. Biol. Soc. p. 5010-3 (2012).

MD Guidelines: hemiplegia. Available from: http://www.mdguidelines.com/hemiplegia, document available on or before Jun. 29, 2009 (per Internet Archive Wayback Machine, http://web.archive.org/web/20090629171340/http://www.mdguidelines.com/hemiplegia), Accessed on Jul. 6, 2015.

Medicaid Reimbursement. Center for Telehealth and e-Health Law; Available from: http://ctel.org/expertise/reimbursement/medicaid-reimbursement/.

Muller-Riemenschneider, F. et al., "Cost-effectiveness of interventions promoting physical activity", Br J Sports Med, 43(1):70-6 (2009).

Office of the Governor, Economic Development & Tourism. The Texas Biotechnology Industry, 2014.

Panteliadis, C., et al., "Congenital hemiplegia. A disease with manifold problems", Nervenarzt, 78(10):1188-94 (2007).

Parmar, A. "U.S. Telehealth Patient Population to Grow to 1.3 Million by 2017 from 227,400", MedCity News, 2013.

Patel, S., et al., "A Novel Approach to Monitor Rehabilitation Outcomes in Stroke Survivors Using Wearable Technology", Proceedings of the IEEE, 98(3):450-461 (2010).

Reimbursement for telehealth services. Practice Central 2011; Available from: http://www.apapracticecentral.org/update/2011/03-31/reimbursement.aspx.

Sanford, J., et al., "Reliability of the Fugl-Meyer assessment for testing motor performance in patients following stroke", Phys. Ther., 73(7):447-54 (1993).

Schnebel, B., et al., "In vivo study of head impacts in football: a comparison of National Collegiate Athletic Association Division I versus high school impacts", Neurosurgery 60(3):490-5; discussion 495-6 (2007).

Stroke Inpatient Rehabilitation Statistics 2011. University of Utah Health Care 2011; Available from: http://healthcare.utah.edu/rehab/About%20Us/outcomes/stroke.html.

Taub, E. et al., "Constraint-induced movement therapy to enhance recovery after stroke", Curr. Atheroscler Rep. 3(4):279-86 (2001).

Taub, E., et al., "Technique to improve chronic motor deficit after stroke", Arch. Phys. Med. Rehabil., 74(4):347-54 (1993).

\* cited by examiner

SYSTEMS AND METHODS FOR SENSORIMOTOR REHABILITATION

CROSS-REFERENCE TO RELATED APPLICATIONS

This application claims the benefit under 35 U.S.C. §119 (e) as a nonprovisional of U.S. Provisional Application No. 61/810,141, titled A WEARABLE SENSOR SYSTEM FOR SENSORIMOTOR REHABILITATION USING INERTIAL MEASUREMENT, and filed Apr. 9, 2013, the entirety of which is incorporated herein by reference and made a part of this specification.

BACKGROUND

1. Field

The present application generally relates to analyzing body movement kinematics of a person, and in particular analyzing the use of limbs to provide feedback for sensorimotor rehabilitation.

2. Description of the Related Art

Stroke is a leading cause of severe long-term disability. Stroke and other causes of central nervous system damage (e.g., spinal cord injury, traumatic brain injury, brain infections, cerebral palsy, demyelinating diseases, meningitis, brain tumors, and congenital brain malformations) can result in a debilitating loss of motor control that is often more pronounced in one limb than the other. As a result of this motor function imbalance, patients tend to stop using their affected (e.g., impaired or relatively more affected/impaired) limb and instead favor the unaffected (e.g., unimpaired or relatively less affected/impaired) limb. Such favored use of a particular limb creates a phenomenon that is referred to as learned non-use where patients can continue to favor their unaffected limb and rehabilitation of the affected limb is compromised. Using or attempting to use the affected limb during activities of daily living, despite considerable difficulty, stimulates neuroplasticity and motor function recovery.

A rehabilitative therapy called Constraint Induced Movement Therapy (CIMT) has been shown to prevent and/or reverse learned non-use following stroke, as discussed in Taub, E. and D. M. Morris, *Constraint-induced movement therapy to enhance recovery after stroke*, Curr Atheroscler Rep, 2001, 3(4): p. 279-86, which is incorporated by reference and made a part of this specification. CIMT has also been more recently explored as a treatment for children with Cerebral Palsy in cases where one limb exhibits less motor impairment than the other, as discussed in Huang, H. H., et al., *Bound for success: a systematic review of constraint-induced movement therapy in children with cerebral palsy supports improved arm and hand use*, Phys Ther, 2009, 89(11): p. 1126-41, which is incorporated by reference and made a part of this specification. CIMT involves constraining the unaffected limb thereby forcing the patient to use their affected limb. Forced use of the affected limb stimulates neuroplasticity and has been shown to significantly improve motor function of the affected limb, as discussed in Wolf, S. L., et al., *Effect of constraint-induced movement therapy on upper extremity function 3 to 9 months after stroke: the EXCITE randomized clinical trial*, JAMA, 2006, 296(17): p. 2095-104, which is incorporated by reference and made a part of this specification. A conventional 2-week bout of CIMT consists of constraining the upper limb for up to 90% of waking hours and participating in one-on-one therapy for up to 6 hours per day, 5 days per week.

SUMMARY

CIMT has not yet been incorporated as part of the standard practice for the rehabilitation of the hemiplegic (or hemiparetic) upper extremity due to several limitations and concerns, as discussed in Viana, R. and R. Teasell, *Barriers to the implementation of constraint-induced movement therapy into practice*, Top Stroke Rehabil, 2012, 19(2): p. 104-14, which is incorporated by reference and made a part of this specification. First, constraining the unaffected limb may be a safety issue, for example, in patients with impaired balance. Second, CIMT therapy can be expensive due to, for example, the duration of one-on-one CIMT therapy. Third, patients may decline to participate due to the intensity of the CIMT therapy. Fourth, high dosage of physical and occupational therapy may not be feasible due to, for example, lack of transportation, geography, or other limiting factors. Modified CIMT was developed to potentially address some of these limitations, but still includes, for example, 3 1-hour therapy sessions per week and 5 hours of limb constraint per day.

Disclosed herein are sensorimotor rehabilitation systems and methods of, for example, using wearable sensors to facilitate sensorimotor rehabilitation. In some embodiments, a wearable sensor (or set of wearable sensors) can incorporate or be based on the concepts of CIMT. The sensorimotor rehabilitation system can include at least one wearable sensor on the left upper limb/extremity (e.g., left arm, including shoulder, upper arm, elbow, forearm, wrist, hand, and/or fingers) and/or at least one wearable sensor on the right upper limb/extremity (e.g., right arm, including shoulder, upper arm, elbow, forearm, wrist, hand and/or fingers). In some embodiments, the sensorimotor rehabilitation system can include one or more wearable sensors positioned on a lower extremity (e.g., leg, shank, foot, etc.). In some embodiments, the one or more wearable sensors can be shaped and sized to have a form factor of a bracelet (e.g., one instrumented or sensor bracelet on each wrist). In some embodiments, the one or more wearable sensors can be shaped and sized to have a form factor of a watch (e.g., one instrumented or sensor watch on each wrist). In some embodiments, one wearable sensor can be shaped and sized to have a form factor of a bracelet and one sensor can be shaped and sized to have a form fact of a watch (e.g., one instrumented or sensor bracelet on one wrist and another one instrumented or sensor watch on the other wrist). In some embodiments, the sensors can be connected to and/or affixed to the hands, forearms, and/or upper-arms of the patient. The sensors can use inertial measurement to monitor the movements of limbs. Monitoring the movement of the limbs can include detecting specific movements (e.g., reaching, writing, eating, performing a prescribed rehabilitative exercise). The sensorimotor rehabilitation system can provide feedback to the wearer (e.g., the patient), physician, clinician, and/or trainer regarding limb movement of the wearer.

The provided feedback can reflect the relative usage of the affected (e.g., hemiplegic or hemiparetic) limb compared to the unaffected limb. In some embodiments, the sensorimotor rehabilitation systems and methods can be used to promote usage of the affected limb to inhibit, prevent, impede and/or reverse learned non-use of the affected limb without compromising safety by, for example, constraining the unaffected limb. In some embodiments, the sensorimotor rehabilitation system can facilitate rehabilitative training in a community setting without the presence of a therapist by, for example, reminding the user to perform a prescribed rehabilitation exercise.

The sensorimotor rehabilitation system can provide unobtrusive integration of the sensors into daily activities. The sensorimotor rehabilitation system can measure use of the affected and unaffected limbs so that timely biofeedback can be provided when natural daily activities are occurring. For example, as a patient performs a goal-directed task with the unaffected limb (e.g., reaching for an object), the sensor on that limb will recognize the movement and then trigger a vibrotactile reminder that the patient should try to use the affected limb. If the movement is critical (e.g., signing a check), the patient can simply ignore the feedback and execute the task with the unaffected limb. If the task is not critical, the gentle reminder may be enough to motivate the patient to attempt the task with the affected limb. In some embodiments, the sensorimotor rehabilitation system may not provide periodic, affected-limb reminders to the patient, particularly during resting activities (e.g., when watching TV) to help avoid potential nuisance and annoyance with the system. During resting activities, the sensorimotor rehabilitation system may otherwise be on standby and/or idle without outputting visual, audible, and/or vibrotactile messages.

Generating feedback information can include generating the feedback information for real time presentation, for example. The generating of the feedback information can further include generating information for use in generating audible and/or tactile (e.g., vibrotactile) feedback to, for example, encourage affected limb use during activities of daily living. The generating of feedback can include reminders to perform daily prescribed rehabilitation exercises in a home environment. The generating of the feedback information can further include generating visual feedback indicative an identified characteristic of movement and a suggested corrective action. The generating of feedback information can include electronically storing the feedback information such that the user and/or therapist can later access the feedback information, providing documentation of progress. For example, if the user is not attempting to use their affected limb during activities of daily living or if the user is not performing prescribed rehabilitation exercises then the therapists or other caregiver would have objective data to provide feedback to patients during follow-up visits. Information gathered from such an assessment can aid therapists in more efficiently targeting at-risk or non-compliant patients.

The sensorimotor rehabilitation system also leverages patient accountability because the therapist, or other caregiver, may have convenient access to activity data via a secure website. In that case, patients who, for example, do not attempt to use the affected limb (e.g., ignore prompts from the sensorimotor rehabilitation system) in the home environment could be reminded to do so at their next clinical visit or other meeting with a caregiver. Through biofeedback and accountability, the sensorimotor rehabilitation system can help inhibit, prevent, and/or reverse learned non-use without compromising safety and overburdening the patient by physically constraining the unaffected limb. Additionally, patients who tend to use both limbs generally exhibit better every-day functioning; yet those patients may still tend to favor the use of the unaffected limb. Therefore, in some cases, encouraging the use of the affected limb may both facilitate motor rehabilitation via neuroplasticity and improve every-day functioning.

Wearable sensors can be used in real time or substantially real time because the recorded signals can be processed quickly. Certain embodiments utilizing a combination of multiple accelerometers, angular rate sensors (gyroscopes), and magnetometers can act as a hybrid kinematic sensor module for measuring the 3D kinematics of different body segments, as well as for various clinical applications such as measuring spatio-temporal parameters of gait, assessing joint kinematics, assessing the risk of falling, and monitoring spontaneous daily physical activity. U.S. Pat. No. 8,206,325, entitled "AMBULATORY SYSTEM FOR MEASURING AND MONITORING PHYSICAL ACTIVITY AND RISK OF FALLING FOR AUTOMATIC FALL DETECTION" (the '325 patent) is hereby incorporated by reference in its entirety herein. Techniques described in the '325 patent, including techniques for assessing gait, determining risk of falling, monitoring physical activity, and the like, are compatible with and can be used in conjunction embodiments described herein.

The inertial sensor(s) can include an accelerometer. In some embodiments, the sensor can include a gyroscope and/or a magnetometer. A tri-axial accelerometer can measure acceleration in three perpendicular directions. A gyroscope can provide data that can be integrated (e.g., over a particular and/or predetermined movement of a body segment) to provide an estimation of orientation of the body segment. A magnetometer can be used to estimate orientation, for example, relative to the earth's magnetic field. In some embodiments, an accelerometer may not be used. In some embodiments, the sensor (e.g., an inertial sensor) may be an accelerometer or a gyroscope or both. The accelerometer and/or the gyroscope can be uni-axial, bi-axial, or tri-axial, for example, measuring acceleration and/or rotational velocity along at least one axis. Accelerometer, gyroscope, and/or magnetometer data may be combined to provide a quaternion representation of the sensor in space corresponding to a position and movement of a body segment. The sensor(s) may be Micro Electrical Mechanical Systems (MEMS) based inertial sensor technology, (e.g., InvenSens MPU-9150). The inertial sensor(s) can be attached to, for example, directly to the person or to another item attached to the person (e.g., clothing and/or band around or about a body segment such as an upper limb).

In some embodiments, a feedback mechanism including information about the wearer's body segment (e.g., upper limb) movement can be used to facilitate automated feedback (e.g., virtual coaching) that guides the user for improved motor function or improved sensorimotor rehabilitation. Automated feedback can be provided in lieu of or in addition to descriptive information related to body segment movement (e.g., quantity and type of movement) where descriptive information may not include feedback (e.g., suggested corrective action) to facilitate sensorimotor rehabilitation.

A method of analyzing limb use can include receiving one or more signals generated by at least one inertial sensor supported at a position on an upper limb of a person. The method can further include, with processing electronics comprising digital logic circuitry, processing sensor data derived from the one or more signals to identify a characteristic associated with the use of the upper limb. Based at least in part on the identified characteristic, the method includes generating information usable to present feedback to the person. The feedback can be indicative of usage of the limb and/or a corrective action for achieving a desired and/or predetermined usage of the limb. In some embodiments, the method is performed using exclusively sensors supported by the person's body.

The inertial sensor and the processing electronics can be housed together in a packaging. The packaging can include an attachment mechanism configured to allow the packaging to be attached to one or more upper limbs or parts of limbs of a person. The inertial sensor may be housed in a packaging comprising an engagement mechanism configured to mate with a mounting unit to releasably secure the packaging to a sensor mount unit attached to the person (e.g., wrist of the person).

In some embodiments, the sensorimotor rehabilitation system can include a wireless transmitter configured to send to a separate computer system the information usable to present the feedback to the user. At least a portion of the processing electronics may reside in a computer system that is separate from a housing that contains the inertial sensor. The sensorimotor rehabilitation system can be configured to perform any of the functionality described above with respect to the method of analyzing limb use, or any limb use analysis and feedback functionality otherwise described herein.

The foregoing is a summary and contains simplifications, generalization, and omissions of detail. Those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of any subject matter described herein.

BRIEF DESCRIPTION OF THE DRAWINGS

The foregoing and other features of the present disclosure will become more fully apparent from the following description, taken in conjunction with the accompanying drawings. Understanding that these drawings depict only some embodiments in accordance with the disclosure and are, therefore, not to be considered limiting of its scope, the disclosure will be described with additional specificity and detail through use of the accompanying drawings.

DETAILED DESCRIPTION

Figure 1:
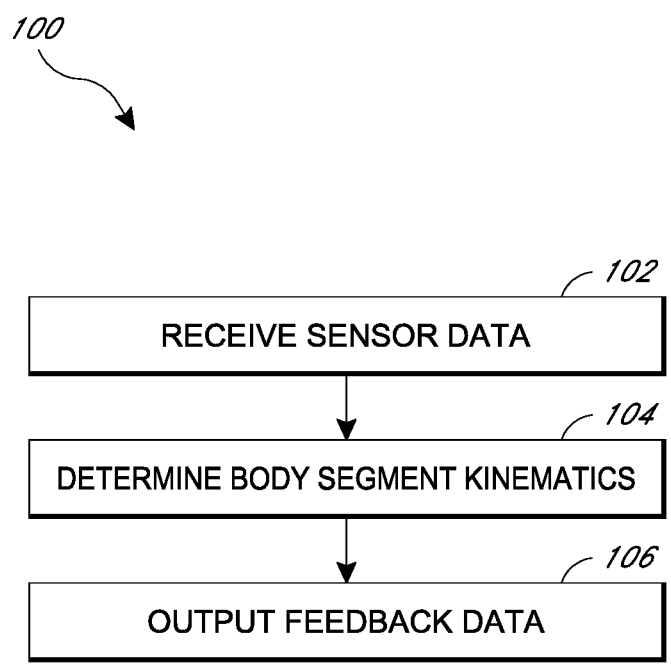
FIG. 1 is a flow diagram illustrating a body segment movement analysis and feedback method in accordance with some embodiments.

In the following detailed description, reference is made to the accompanying drawings, which form a part hereof. In the drawings, similar symbols typically identify similar components, unless context dictates otherwise. The illustrative embodiments described in the detailed description and drawings are not meant to be limiting. Other embodiments may be utilized, and other changes may be made, without departing from the spirit or scope of the subject matter presented here. It will be readily understood that the aspects of the present disclosure, as generally described herein, and illustrated in the figures, may be arranged, substituted, combined, and designed in a wide variety of different configurations, all of which are explicitly contemplated and made a part of this disclosure.

In particular, disclosed herein are systems and methods for analyzing body segment kinematics/movement (e.g., predetermined clinically relevant biomechanical parameters of limb movement) to help improve sensorimotor rehabilitation (e.g., help improve motor function).

Until recently, measurement of body motion under real-life conditions has been difficult and impractical. Traditionally, limb movement has been assessed using laboratory-based systems (e.g., during clinical visits). While these systems are clinically accepted as "the gold standard," several drawbacks render them unsuitable for clinical and/or everyday applications. Specifically, currently-available motion-analysis systems are time-consuming, expensive, and require an existing infrastructure and highly-trained personnel.

The recent emergence of body-worn sensor technology has provided new ways to measure and assess motor functions, including body kinematics (e.g., limb movement) and physical activity. For example, the combination of accelerometers with angular-rate sensors (e.g., gyroscopes) holds great promise for hybrid kinematic sensor modules that measure the three-dimensional kinematics of body segments. Three key advantages render body-worn sensors ideal tools for developing clinical, sports, and/or everyday applications: 1) they are relatively inexpensive; 2) they are light-weight and portable; and 3) they typically do not require a specific environment or installation of any particular infrastructure. Body-worn sensors consequently have tremendous potential for enabling physicians and/or trainers to evaluate body movement under real conditions by quantifying its subcomponents, such as body-segment kinematics data, kinetic data, and motor adaptation.

Sensorimotor Rehabilitation Overview

Embodiments of the disclosure are directed to an innovative, portable, and cost-effective body-worn sensor-based system to evaluate body segment kinematics, and in particular, movement of body segments such as limb movement. Various embodiments use accelerometers, gyroscopes, and/or magnetometers to measure the three-dimensional motion of, for example, upper limb of a person. In some embodiments, sensors could be attached to other body segments to evaluate a person's body segment movements and/or provide feedback for sensorimotor rehabilitation. In some embodiments, the sensorimotor rehabilitation system can include one or more of the following: 1) a sensing unit(s) (e.g., inertial sensor) that can be affixed, attached, and/or connected to the arm, including shoulder, upper arm, elbow, forearm, wrist, hand, and/or fingers, and/or 2) a unit that provides feedback, which may be provided through a variety of channels such as, for example, directly by the sensor or indirectly via an external electronic device (e.g., personal computer, mobile phone, tablet computer, and/or other device, some of which may be carried by the user). In some embodiments, a method for sensorimotor rehabilitation analysis can include one or more of the following: 1) method(s) for computing or extracting relevant body segment kinematics from data recorded by the sensing unit, and/or 2) method(s) for generating feedback information based on the recorded data for display of that information to the user(s). Users of the system may include the person wearing the sensor(s) or other individuals assigned to view the wearer(s) data (e.g., a trainer or medical personnel).

To enable unsupervised (e.g., by a therapist) monitoring of motor activity in home and community settings, the sensorimotor rehabilitation system can perform automatic detection of goal-directed movements (e.g., reaching for a glass of water, turning a door knob and/or performing a prescribed therapeutic exercises) during activities of daily living (ADL). Therapists can remotely monitor the movement data and/or review the data with patients during clinic visits.

FIG. 1 is a flow diagram illustrating a body segment movement analysis (e.g., motor function analysis) and feedback method 100 in accordance with some embodiments. At block 102, sensor data as discussed herein is received. The sensor data may include data collected from sensor(s) worn by a person during body movement. At block 104, the sensorimotor rehabilitation system may determine body segment kinematics data including quantity and type of limb movement. The term "determine" as used herein should be broadly interpreted to mean any method of determining the body segment kinematics data, including deriving the body segment kinematics data as well as estimating the body segment kinematics data.

At block 106, in some embodiments, feedback data is generated and outputted by the sensorimotor rehabilitation system. In some embodiments, the feedback data can include information sufficient to generate depiction of desired feedback for display via a user interface display. The feedback data can include a comparison of a determined quantity and type of limb movement or other characteristics with a desired quantity and type of limb movement or other characteristics. The desired quantity and type of limb movement may be determined based on sensor data collected when the user is in motion. The feedback data can be provided for real time display to a user. In some embodiments, the body segment kinematics and/or feedback data may be stored in a mass storage within the system or remotely on a server and accessed for later viewing. The stored body segment kinematics and/or feedback data may be combined with data related to a future performance of motion to support data tracking and analysis for desired and/or predetermined body segment kinematics for sensorimotor rehabilitation.

The sensorimotor rehabilitation system can be developed to be applicable generally to hemiparetic patients. In some embodiments, the sensorimotor rehabilitation system can be tailored to a specific patient or specific set of patients. For example, the sensorimotor system can have a configuration mode where the patient performs a specific set of body motions and/or exercises for the sensorimotor rehabilitation system to learn movements of the patient. In some embodiments, the sensorimotor rehabilitation system can be adjusted to function for a specific set of patients. For example, a patient and/or physician may input specified data and/or ranges for data into the sensorimotor rehabilitation system via, for example, a configuration mode. The input data and/or ranges of data can include, for example, height, weight, arm length, level of arm function, clinical movement scores (e.g., Functional Ability Scale (FAS) score as discussed in Wolf, S., et al., *Pilot normative database for the Wolf Motor Function Test*, Archives of Physical Medicine and rehabilitation, 2006: p. 443-5, which is incorporated by reference and made a part of this specification, or Fugl-Meyer Assessment score as discussed in Sanford, J., et al., *Reliability of the Fugl-Meyer assessment for testing motor performance in patients following stroke*, Phys Ther, 1993, 73(7): p. 447-54, which is incorporated by reference and made a part of this specification), affected limb side (i.e., left or right), etc. The input data can also include a set of home exercises to be performed each day, and the wearable sensor system can be used to monitor compliance with prescribed exercises. In some embodiments a set of home exercises could selected from preset options including, for example, those listed in Table 1.

TABLE 1

Upper-Extremity Rehabilitation Exercises

| Exercise Type | Tasks |
| --- | --- |
| Strength | Sagittal plane arm raises |
| | Coronal plane arm raises |
| | Elbow flexion/extension |
| | Thera-Band pulls |
| Range of Motion | Affected hand to contralateral ear |
| | Supine arm raises (toward ceiling) |
| | Wrist pronation / supination |
| | Wrist flexion / extension |
| Functional | Wrap fingers around a handle (e.g., refrigerator) and pull to open door |
| | Reach for and toggle a light switch |
| | Make smooth circular motions (e.g., polishing a tabletop) |
| | Put small objects in, and take them out, of a bin |
| | Turn pages in a book or magazine |

Sensorimotor Rehabilitation Sensors

Figure 2:
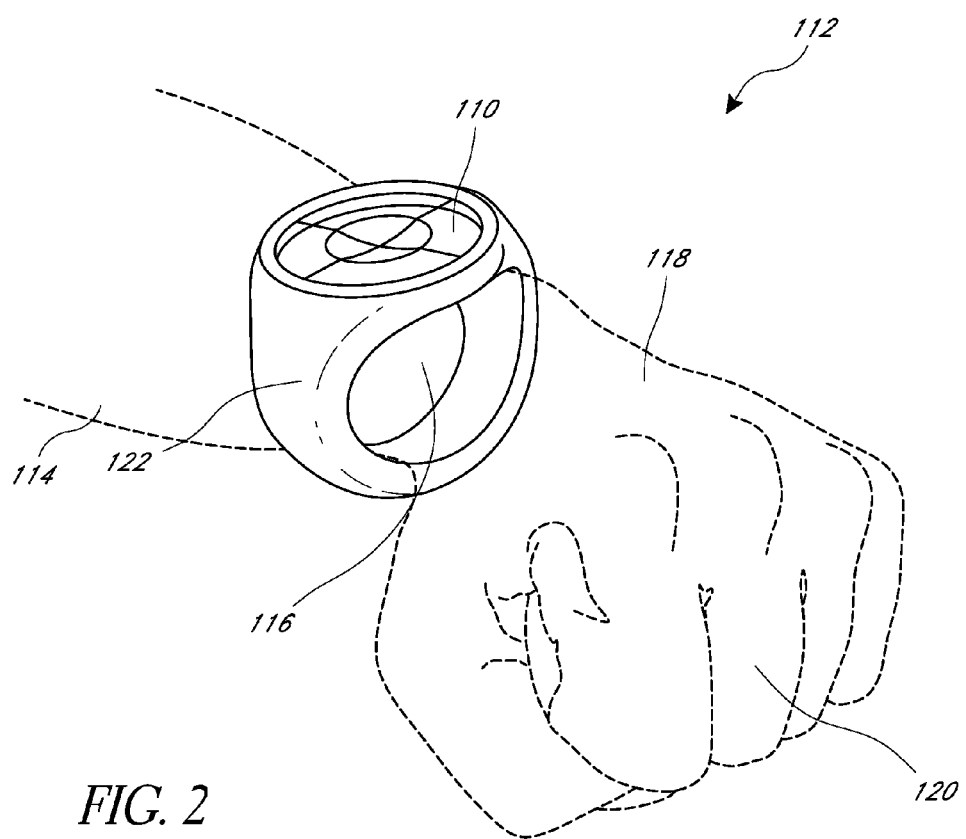
FIG. 2 illustrates an example embodiment of a sensor on an upper limb.

FIG. 2 illustrates an example embodiment of a sensor 110 (e.g., inertial sensor) on an upper limb (e.g. arm) 112. As illustrated in FIG. 2, the sensor 110 can be affixed, attached, and/or connected to a forearm 114 and/or wrist 116 of a person. In some embodiments, the sensor 110 can be affixed, attached, and/or connected to a forearm 114, wrist 116, hand 118, and/or finger(s) 120, including upper arm and/or shoulder as discussed herein. The sensor 110 can be embedded, affixed, attached, and/or connected to a band 122. The band 122 can be made of any suitable flexible, elastic, and/or rigid plastic or rubber (e.g., silicone) to position the sensor 110 on a body part of a person as discussed herein. The band 122 can house and position the sensor 110 in a desired and/or predetermined position. The band 122 can be sized and shaped envelope, wrap, affix, attach, and/or connect to body parts, (e.g., upper limb 112). As illustrated in FIG. 2, the sensor 110 can have a form factor of a wristband and/or bracelet. In some embodiments, the sensor 110 can be integrated with other wearable items (e.g., clothing) to attain the features and functionality of the sensorimotor rehabilitation system as discussed herein.

Figure 3:
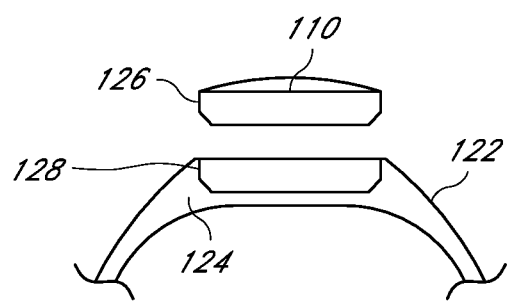
FIG. 3 illustrates an example embodiment of a sensor.

FIG. 3 illustrates an example embodiment of a sensor 110 with a base (e.g., a mounting bracket) 124. The sensor 110 can include a packaging that contains one or more inertial sensors (e.g., accelerometers of gyroscopes) and/or other types of sensors (e.g., magnetometers) as discussed herein. The sensor 110 can further include processing electronics or other appropriate componentry for processing data received from the sensor in any of the manners discussed herein. The sensor 110 can have attachment mechanisms to attach to various body parts and/or outerwear of a person as discussed herein. The sensor 110 can be removable from a base or clip 124. As illustrated in FIG. 3, a base 124 can be sized and shaped to engage a sensor 110. The base 124 can connect to, engage with, and/or mate with the sensor 110 to house the sensor 110 in a desired and/or predetermined position. The base 124 can connect to, engage with, and/or mate with various body parts or outerwear of a person as discussed herein in a desired position. As illustrated in FIG. 3, the base 124 can connect to and/or be integrated into a band 122. The base 124 can have interlocking features to position the sensor 110 in a desired position relative to the base 124. For example, the sensor 110 and base 124 can be held together with, for example, interference fit mechanisms, snap fit mechanisms, and so forth, which can include using male and female mating parts (e.g., tongue-and-groove corresponding parts). As illustrated in FIG. 3, the sensor 110 can have a protrusion or projection 126.

The base 124 can have a corresponding recess or groove 128. The sensor 110 can be positioned and "snap" into place within the base 124 when the protrusion 126 mates and/or engages with the recess 128. In some embodiments, the sensor 110 can be permanently or non-removeably integrated into the band 122.

In some embodiments, specially designed clothing (e.g., sleeves, shirts, gloves, etc.) can be made to house the sensor 110 in a predetermined/desired position. For example, a sleeve of a shirt may have an indentation or cutout to house the sensor 110 in a desired and/or predetermined position. Other configurations can be implemented for other clothing of the user. For example, the sensor 110 can be adapted to attach to pre-existing everyday clothing (e.g., with bands, Velcro, laces, brackets, etc.). Housing the sensor 110 in a predetermined position relative to a body segment of a user may allow for more accurate and/or precise measurement of body movement as discussed herein.

Figure 4:
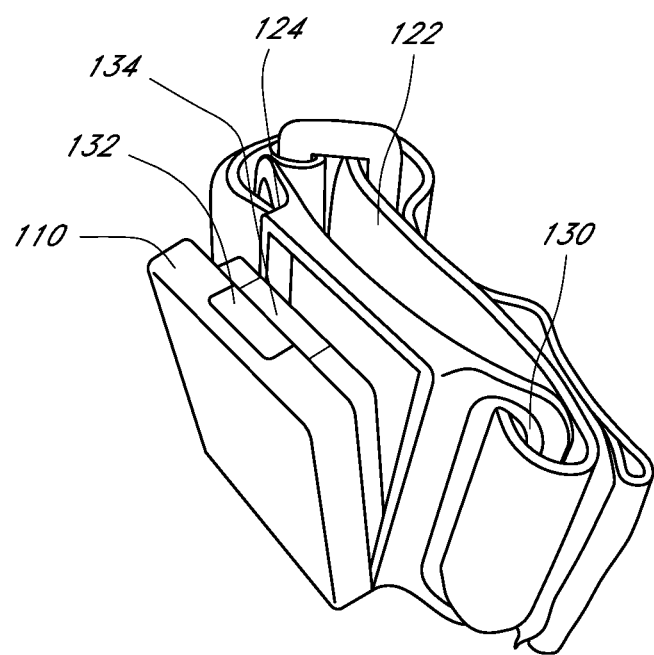
FIG. 4 illustrates another example embodiment of a sensor.

FIG. 4 illustrates another example embodiment of a sensor 110 that cooperates and mounts to a base 124 having a band (e.g., a strap) 122 for attaching to a person. For example, in some embodiments, the base 124 can have openings 130. The openings 130 can be sized and shaped to accept the band 122 that wraps around a part of an upper limb 112 and/or other body part of a person. The sensor 110 includes a packaging that contains one or more inertial sensors (e.g., accelerometers of gyroscopes) and/or other types sensors (e.g., magnetometers), as discussed herein. The sensor 110 can further include processing electronics or other appropriate componentry for processing data received from the sensor in any of the manners discussed herein. The base 124 includes a cut-out dimensioned to accept the sensor 110. The sensor 110 and base 124 can each include appropriate mechanical features for snapping the sensor 110 into place in the base 123, for example. The sensor 110 in the illustrated embodiment includes a button 132 which, when depressed, causes movement of a release member 134, which releases the sensor 110 from the base 124. In some embodiments, the base 124 includes the button 132 and release member 134 instead of the sensor 110. The strap 122 can be particularly useful for positioning and tightening around the person's upper arm (e.g., around the person's sleeve), but can also be used to secure the combined sensor 110 and base 124 around the forearm 114, around the wrist 116, around the hand 118, etc.

In some embodiments, the sensor 110 can have an Analog Devices ADXL344 tri-axial accelerometer, Nordic Semiconductor nRF51822 BLE radio module, a main controller, and/or a low power vibrotactor as discussed herein. A printed circuit board (PCB) with components of the sensor 110 as discussed herein can be housed in a flexible over-molded silicone (or other suitable material) enclosure.

Figure 5:
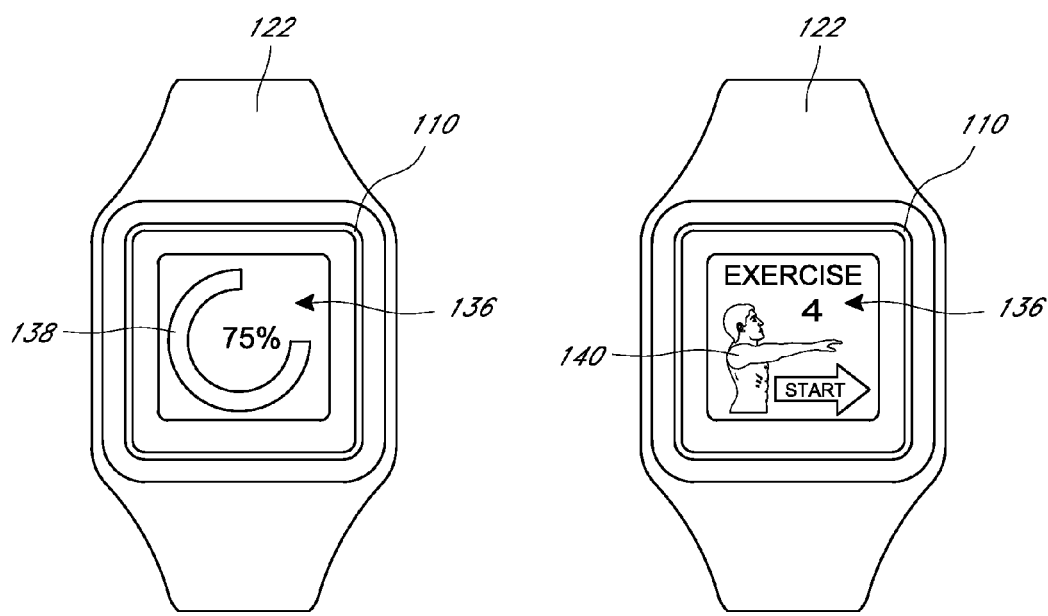
FIG. 5 illustrates another example embodiment of a sensor.

FIG. 5 illustrates another example embodiment of a sensor 110 that, for example, has a form factor of a watch. The sensor 110 can have a strap 122 for affixing the sensor 110 to a person as discussed herein. The sensor 110 can have a visual display 136 for providing visual feedback as discussed herein. The watch sensor 110 can also provide tactile feedback as discussed herein. As illustrated in FIG. 5, the visual display 136 can provide a limb usage graphic 138 (e.g., illustrating quantity or relative quantity of limb movement). The limb usage display 138 can communicate to a user the relative usage of an affected versus unaffected limb. For example, as illustrated in FIG. 5, the limb usage graphic 138 illustrates that a patient has used his/her affected limb 75% of the time during a predetermined time or activity period. The limb usage display 138 can change/update dynamically during activity in real time and/or update at predetermined periods of time and/or activity. For example, a target ratio of affected to unaffected limb use could be set by the patient and/or therapist as the goal for a certain hour, day, week, month, etc. Patients can then visually track his/her progress toward achieving that goal continuously and in real time.

As illustrated in FIG. 5, the visual display 136 can provide an exercise graphic 140. The exercise graphic 140 can prompt and/or remind a patient to start a particular and/or predetermined exercise or other movement. For example, as illustrated in FIG. 5, the exercise graphic 140 illustrates that a patient should start an upper limb 112 raising and/or reaching exercise. The exercise graphic 140 can be interactive and/or dynamically display sequences of exercises to be performed. The sensor 110 can track, monitor, and/or analyze an exercise being performed in real time. The visual display 136 can provide feedback as discussed herein on the exercise as performed in real time or after performance of the exercise.

In some embodiments, the watch sensor 110 can be integrated into a commercially available programmable smartwatch with a Bluetooth Low Energy (BLE) radio module (e.g., STRATA Stealth, Meta Watch Ltd., Dallas, Tex.). For example, a STRATA Stealth watch can have a tri-axial accelerometer, vibrotactor, BLE radio module, programmable display, and/or microprocessor that can be modified and/or configured to have the features and functions of a sensor 110 as discussed herein.

With a sensor 110 as discussed herein, the sensorimotor rehabilitation system can provide real time visual, audible, and/or vibrotactile feedback to encourage affected limb use during activities of daily living. The sensorimotor rehabilitation system can provide reminders to perform daily prescribed motor control exercises in the home environment. To provide one or more features and function as discussed herein, the sensor 110 can perform one or more of the following: 1) analyze acceleration data and/or other body segment movement data in real time; 2) store acceleration/movement data in an on-board memory; 3) receive acceleration/movement data from another sensor 110 worn, for example, on a corresponding upper limb 112 of the person; 4) output acceleration/movement data to a wired and/or wireless external receiver (e.g., base station 310 as discussed herein, see FIG. 8); and/or 5) initiate visual and/or vibrotactile biofeedback according to desired and/or predetermined feedback as discussed herein.

In some embodiments, the sensor 110 can have battery capacity and/or low energy consuming components to achieve sustainable monitoring of patient body segment for a day or more, a week or more, or a month or more without recharging. The sensor 110 may remain on standby and/or (e.g., not record movement data) until body movement is detected by the sensor 110 as discussed herein. Such sustainable periods of function without recharging can allow the user to continuously (e.g., during awake periods) wear the sensor 110 without recharging. The sensors 110 can be recharged at a home of a patient and/or during clinic visits. Recharging only during clinic visits can help increase patient compliance (e.g., continuously wearing the sensor 110) where, for example, the sensor 110 is removed from the patient primarily during clinic visits and recharged by a clinician during the clinic visit.

Figure 8:
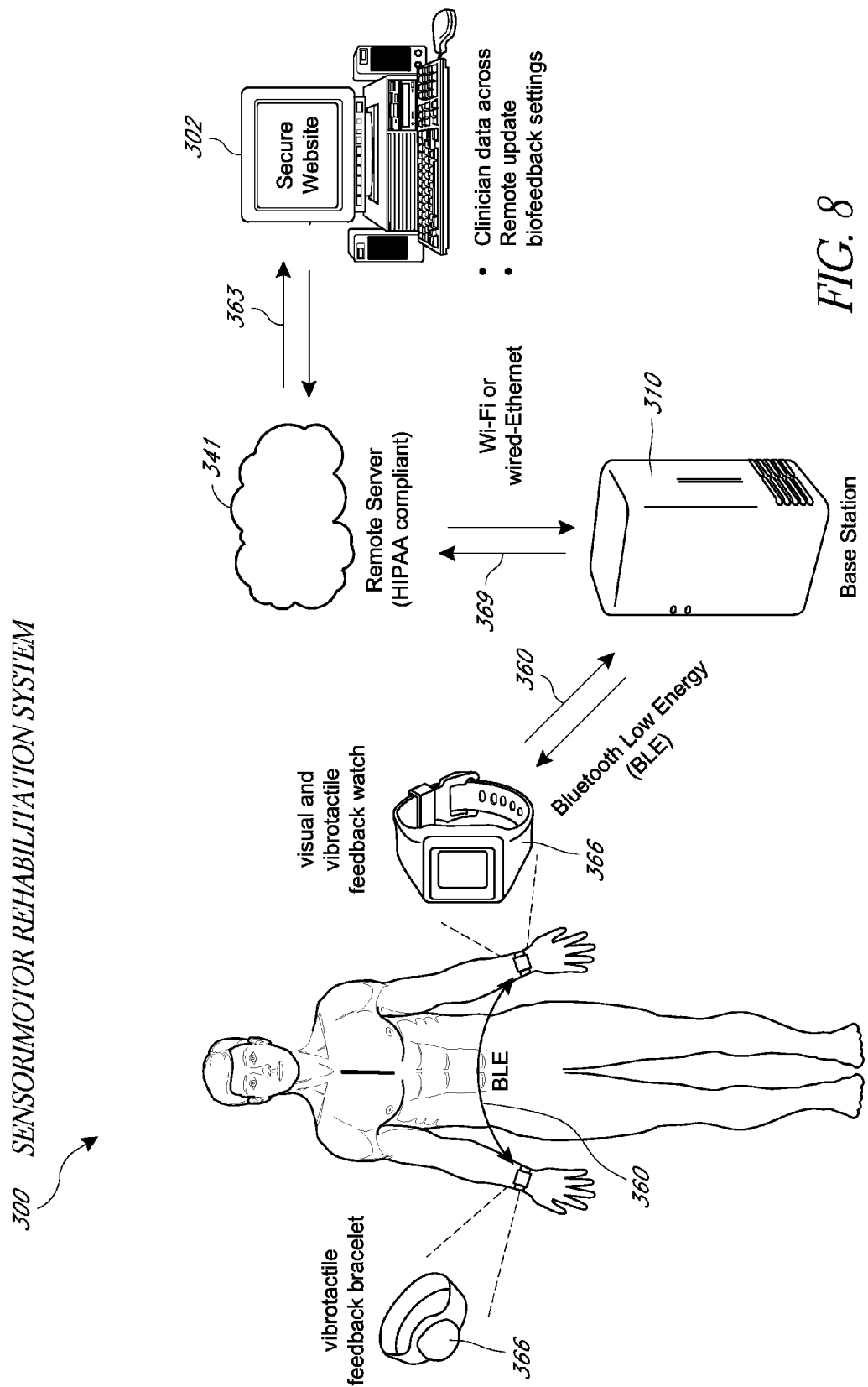
FIG. 8 illustrates an example embodiment of a sensorimotor rehabilitation system.

In some embodiments, the sensorimotor rehabilitation system can have two or more wearable sensors 110 (e.g., a sensor 110 on each upper limb 112 of a person), as for example, illustrated in FIG. 8. The two or more sensors 110 can wirelessly and/or via wires communicate with each other and/or other sensorimotor rehabilitation system components as discussed herein. Each sensor 110 can have one or more acceleration sensors and/or one or more tilt sensors. In some embodiments, the wearable sensors 110 can have a tri-axial accelerometer measuring acceleration in three perpendicular directions. In some embodiments, the sensor 110 can include one or more rotational velocity sensors (e.g., gyroscopes) and/or one or more magnetic field sensors (e.g., magnetometers). The various combinations of sensors as discussed herein can be an inertial sensor package (e.g., sensor 110) as discussed herein. The two or more wearable sensors 110 can include any combination of sensor forms as discussed herein. For example, at least one of the sensors 110 can have a visual display 136 as discussed herein (e.g., a sensor 110 having a watch form) while the other sensors 110 will not having a visual display 136. As another example, the two or more sensors 110 can be without visual displays 136 (e.g., a sensor 110 having a wristband/bracelet form) and provide vibrotactile feedback as discussed herein.

According to some embodiments herein, the biofeedback watch and/or biofeedback bracelet sensors 110 can be positioned on contralateral wrists 116, can monitor movements of the affected and unaffected limbs 112, and/or can provide visual, audible, and/or vibrotactile feedback to the user as discussed herein. In some embodiments, the biofeedback watch sensor 110 can be worn on the affected limb 112. In some embodiments, the biofeedback watch sensor 110 can be worn on the unaffected limb 112. The biofeedback watch 110 can provide the user with desired visual feedback about use of, for example, the affected limb, as well as display, for example, reminders about home-based exercises prescribed by a clinician.

Monitoring and Analysis of Body Segment Movement

In some embodiments, monitoring the use of a body segment, such as a particular limb (e.g., upper limb 112) can include detecting specific movements (e.g., reaching, writing, eating, performing prescribed rehabilitative exercises) based on measurements via the sensor 110 as discussed herein. In some embodiments, monitoring the use of a body segment, such as a particular limb (e.g., upper limb 112) can include detecting specific types of movements. In some embodiments, detecting specific types of movements can included distinguishing goal-directed upper-extremity movements (e.g., reaching for an object) from secondary or non-goal directed movements (e.g., the arms swinging as a result of torso movement or during walking, or other sources of noise). In some embodiments, activities of daily living (ADL) can be categorized and/or grouped into predetermined types of body movements and/or groups of types of body movements (e.g., Table 1). The sensorimotor rehabilitation system may monitor and provide feedback based on a number of types of body movements and/or groups of types of body movements (e.g., quantity of unimanual movements or quantity of reaching movements of the person). The sensorimotor rehabilitation system may provide feedback that includes, for example, a number of types of body movements and/or groups of types of body movements rather than basing feedback on the quantity of limb movement of all (e.g., types) of body movements.

TABLE 2

Examples of types of upper-extremity ADL movements

| ADL Types (Example 1) | ADL Types (Example 2) | Tasks |
|---|---|---|
| Goal Directed | Unimanual | Drinking a glass of water<br>Erasing a whiteboard<br>Opening a door<br>Brushing hair |

TABLE 2-continued

Examples of types of upper-extremity ADL movements

| ADL Types (Example 1) | ADL Types (Example 2) | Tasks |
|---|---|---|
| Goal Directed | Bimanual | Pick up a pen and remove the cap<br>Pick-up and place a two-handled basket (e.g., laundry basket)<br>Put a table cloth on a table<br>Apply toothpaste to a toothbrush |
| Goal Directed | Stabilization | Stabilize a jar while opening it<br>Hold paper in place while writing<br>Carry a light object by supporting it against the body |
| Non Goal Directed | Secondary | Walking<br>Standing and rotating torso<br>Stand-to-sit transitions WITHOUT using arm for bracing |

Specific movements or types of movements can be identified using one or more of the following methods: 1) estimating upper limb kinematics from measured inertial data and identifying movement type based on the estimated upper limb kinematics (e.g., kinematic methods); 2) applying classification rules (e.g., classification approaches) to the measured inertial data, wherein the classification rules have been determined using artificial intelligence classification methods (e.g., machine learning) or statistical classification methods (e.g., Bayesian classification); or 3) using a combination of kinematic and classification approaches.

A kinematic method could, for example, include combining accelerometer, gyroscope, and/or magnetometer data from a sensor or sensors to provide a quaternion representation of an upper extremity limb segment or segments in space, which could then be used to identify a specific movement (e.g., a reaching task could consist of elbow extension and shoulder flexion). A classification method could, for example, include extracting a set of features from a time period of recorded inertial data by, for example performing any one or more of the following: numerical integration, differentiation, linear combinations, non-linear combinations, time frequency transforms, and the like. These features could then serve as input to an algorithm whose output is a movement type or category, wherein said algorithm was developed (e.g., trained) based on a data set of inertial sensors signals corresponding to known movement types or categories (e.g., training dataset).

As an example, this training data set could consist of data from inertial sensors that were collected while subjects in a research study wore the sensors on their upper extremities and performed activities of daily living (e.g., those listed in Table 1) or performed upper extremity exercises (e.g., those listed in Table 2). In some embodiments, during algorithm development, a set of features could be extracted from the sensor data captured during laboratory data collections using, for example, a sliding window of time. In some embodiments, for algorithm development, a set or subset of features could be extracted by, for example, performing feature selection using attribute estimators such as, the ReliefF algorithm, as discussed in Robnik-Sikonja, M. and I. Kononenko, *Theoretical and empirical analysis of ReliefF and RReliefF*, Machine Learning Journal, 2003, 53: p. 23-69, which is incorporated by reference and made a part of this specification, mutual information filtering techniques, as discussed in Kraskov, A. et al., *Heirarchical Clustering Using on Mutual Information*, Europhysics Letters, 2005, 70: 278-284, which is incorporated by reference and made a part of this specification, correlation filtering techniques, such as Principal Components Analysis, search approaches, such as Simulated Annealing, as discussed in Kirkpatrick, S., et. al., *Optimization by Simulated Annealing*, Science, 1983, 220: p. 671-80, which is incorporated by reference and made a part of this specification, and other methods.

Continuing with the example, a set or subset of features, along with the training data, could be used to develop binary classifiers to, for example, distinguish goal-directed from non-goal-directed movements, or multi-class classifies to, for example, group movements into categories (e.g., unimanual, bimanual, stabilization, and secondary). The criterion for training the classifier could be, for example, 70%, 80%, 90%, 95%, 99%, or 99.9%, including the foregoing values and ranges bordering therein, recognition rate. The binary or multi-class classifiers could, for example, be developed using artificial intelligence classification methods (e.g., machine learning), such as a Random Forest algorithm, as discussed in Breiman, L., *Random Forest, Machine Learning*, 2001, 45: p. 5-32, which is incorporated by reference and made a part of this specification, or using statistical classification methods, such as Bayesian classification. During algorithm development, the accuracy of the classifiers could be evaluated by performing, for example, a 10-fold cross validation.

In some embodiments, monitoring the use of each limb can include a global measure of limb movement over a time period that is not related to specific movements. A global measure of limb movement could be, for example, the number of peaks in an acceleration signal exceeding a threshold in a given time period. The time period could include about a month, a week, 4 days, 2 days, a day, including about 12 hours or less 6 hours or less, 5 hours or less, 4 hours or less, 3 hours or less, 2 hours or less, 1 hour or less, 30 minutes or less, 15 minutes or less, or 10 minutes or less, including about 9, 8, 7, 6, 5, 4, 3, 2, or 1 minute or less, including the foregoing values and ranges bordering therein.

Motor Function Feedback

In some embodiments, feedback (e.g., biofeedback) can be provided to users regarding body segment movement of a person wearing one or more sensors 110. Users of the sensorimotor rehabilitation system may include the person wearing one or more sensor 110 or other individuals assigned to view the wearer's data (e.g., a therapist, clinician, trainer, caregiver, or other medical personnel). Feedback may be provided through a variety of channels, such as, for example, directly by the sensor 110 or indirectly via an external electronic device (e.g., a personal computer, mobile phone, tablet computer or other device carried by the user). In some embodiments, the body segment movement data and/or feedback data may be housed in a computer server and accessible online via, for example, a website as discussed herein.

The feedback can include encouraging the use of the affected limb. Feedback can include one or more predetermined threshold values (or ranges of values) as discussed herein, indicating desired and/or predetermined body segment movement. In some embodiments, the feedback can be provided directly to the user from the sensor via audible indicators (e.g., sounds), vibrations of the sensor 110, and/or visual indicators generated by the sensor 110 and/or external electronic device. For example, each time the unaffected limb is used, the sensor 110 on the unaffected limb could vibrate or make an unpleasant sound to discourage use of the unaffected limb and encourage use of the affected limb. The feedback can be modified based on the type of movement detected. For example, if the unaffected limb is used in a bimanual task (e.g., picking up a large object) or if the movement of the unaffected limb is secondary or non-goal directed (e.g., the arms swinging as a result of torso movement or during walking) then the feedback could be different or could be eliminated. Vibration can include any suitable tactile feedback device and method, including various patterns of vibrations to convey a predetermined feedback message. Audible indicators may include spoken voice recordings or a computer generated voice reminding the patient to use the affected limb and/or that the unaffected limb is being used. In some embodiments, the external electronic device can include a personal computer, mobile phone, tablet computer, watch, electronics-equipped wrist band, and/or other device carried by the user.

In some embodiments, the sensorimotor rehabilitation system can be configured to discourage any or substantially all use of the unaffected limb (e.g., by providing negative feedback whenever the unaffected limb is used). In some embodiments, the desired ratio of unaffected limb usage to affected limb usage can be tuned or modified so that as the patient becomes more confident in the use of the affected limb, the patient is given feedback to increase the use of the unaffected limb (e.g., not discouraging any or substantially all use of the unaffected limb). For example, the sensorimotor rehabilitation system can provide feedback to direct, guide, and/or encourage use of the limbs at a desired and/or predetermined ratio (e.g., equally or 50/50). Continuing with the example, negative feedback could be delivered if, for example, the patient had made 10 consecutive reaching movements with the unaffected limb without using the affected limb.

Tuning, modifying, and/or changing the desired ratio of unaffected limb usage to affected limb usage can facilitate prolonged biofeedback usage (e.g., for several months or more) of the sensorimotor rehabilitation system after an initial prescribed period of, for example, extremely limited usage of the unaffected limb (e.g., 2 weeks). As discussed herein, patients who tend to use both limbs tend to exhibit better every-day functioning; yet many patients still tend to favor the exclusive use of the unaffected limb as discussed in Haaland, K. Y., et al., *Relationship between arm usage and instrumental activities of daily living after unilateral stroke*, Arch Phys Med Rehabil, 2012, 93(11): p. 1957-62, which is incorporated by reference and made a part of this specification. Therefore, in some cases, encouraging the use of the affected limb may both facilitate motor rehabilitation via neuroplasticity and improve every-day functioning.

In some embodiments, to initiate a daily exercise session a user can push a button on one or more of the sensors 110 and/or select an option on, for example, the graphical display 136, which can be a touch screen. If daily exercises have not been initiated by, for example, 6 PM, a reminder message will be displayed on, for example, the graphical display 136. In some embodiments, the reminder message can be a communicated as an audible and/or vibrotactile message. When the patient initiates the exercise routine, the sensor 110 with a graphical display 136 and/or external device with a display can automatically progress through a therapist specified sequence of prescribed tasks as, for example, movement data is logged as discussed herein.

In some embodiments, the movement data and/or movement descriptors can be processed to quantify and qualify body movement as discussed herein by the sensor 110 itself (e.g., with a processor and memory) and in some embodiments, followed by transmission of the movement data and/or movement descriptors to an external electronic device. In some embodiments, the sensor 110 can transmit raw (unprocessed) data to the external electronic device prior for processing and determination of movement data and/or movement descriptors by software running on the electronic device. The sensor 110 and/or external electronic device can display the processed data to the user along with feedback and instructions regarding specific changes that the user should make for sensorimotor rehabilitation. Data transmission maybe wireless and/or the sensor 110 may be directly docked or connected (e.g., via USB) to the external electronic device for data offload.

Figure 6:
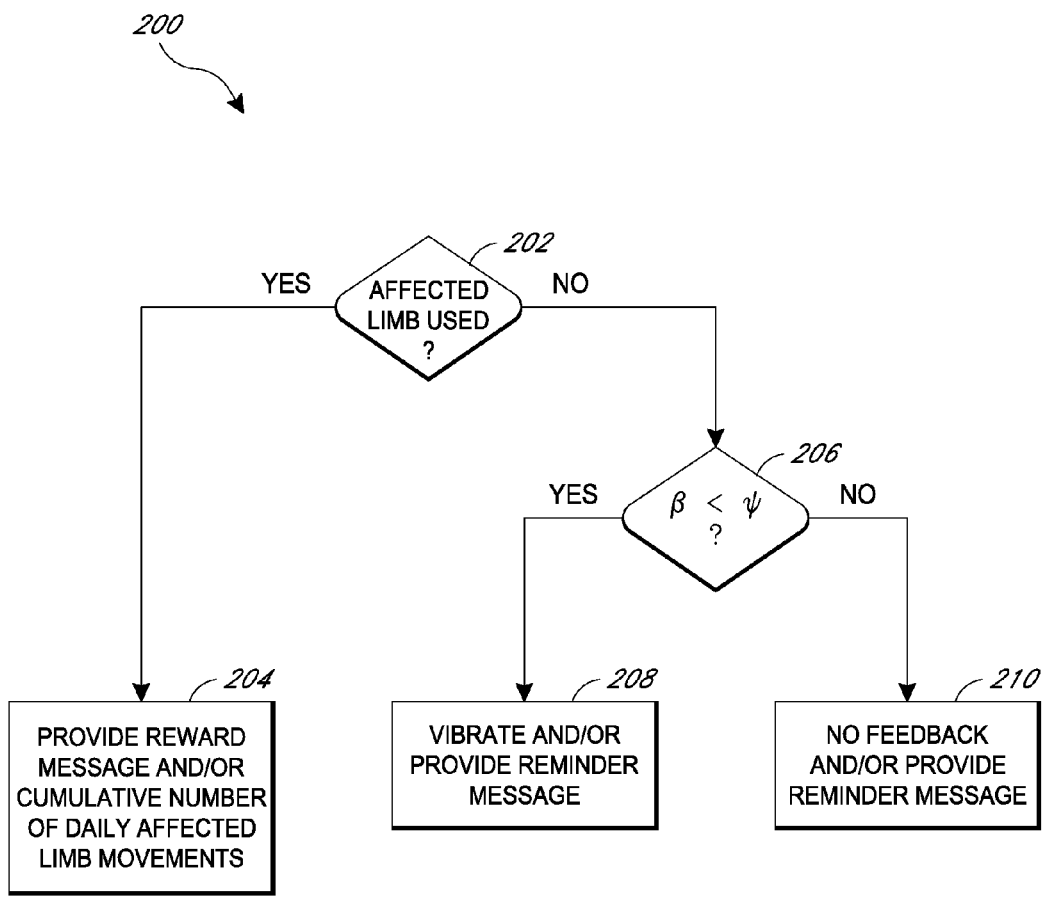
FIG. 6 is a flow diagram illustrating a feedback method in accordance with some embodiments.

FIG. 6 is a flow diagram illustrating a feedback method 200 in accordance with some embodiments. The feedback method 200 can be implemented for real time feedback during activities of daily living as discussed herein. The feedback method 200 can include the utilization of two or more sensors 110 as discussed herein, for example, a first sensor 110 having a watch form and a second sensor 110 having a bracelet form. The biofeedback method 200 can be used during activities of daily living to encourage use of the affected limb during naturally occurring tasks. The biofeedback method 200 can be used during prescribed daily exercises. The biofeedback method 200 can be based on predetermined rules during activities of daily living based on, for example, two predetermined values: the desired and/or predetermined (e.g., specified by the therapist remotely or during a clinical visit) ratio of affected to unaffected limb use ($\Psi$) and the actual ratio of affected to unaffected limb use ($\beta$). $\beta$ can be updated by wireless packet transmission between the watch sensor 110 and bracelet sensor 110. $\beta$ can be updated each time a goal-directed movement is detected or can be updated at a set interval, for example, about every hour, 30 minutes, 15 minutes, 10 minutes, 5, minutes, 1 minute, 30 seconds, 15 seconds, 10 seconds, 5 seconds, or 1 second, including the foregoing values and ranges bordering therein. In some embodiments, $\beta$ is updated and/or determined by one or more of the sensors 110. In some embodiments, movement data is sent to an external device as discussed herein and $\beta$ is updated and/or determined by the external device.

As illustrated in FIG. 6, at step 202, it is determined whether the affected limb is used. If the affected limb is used, at block 204, the user can receive a reward message. The reward message can be displayed to the user on, for example, the graphical display 136 and/or can be communicated via audible and/or vibrotactile messages. In some embodiments, a cumulative number of daily affected limb movements can be displayed on, for example, the graphical display 136 at block 204. The sensor 110 having a watch form can be worn on the affected limb to help a user associate the cumulative usage number displayed with, for example, the affected limb.

If the affected limb is not used, at step 206, it is determined whether the actual ratio of affected to unaffected limb use ($\beta$) is less than the desired and/or predetermined ratio of affected to unaffected limb use ($\Psi$). If $\beta$ is less than $\Psi$, at block 208, one or more of the sensors 110 may provide an audible and/or vibrotactile message to remind or encourage the patient to use the affected limb and/or remind or encourage the patient not to use the unaffected limb. The sensor 110 having a bracelet form can be worn on the unaffected limb to, for example, vibrate when the unaffected limb is not used and $\beta$ is less than $\Psi$ as a deterrent message for using the affected limb or to vibrate when the unaffected limb is used as an encouragement for using the unaffected limb. In some embodiments, a reminder message can be displayed on, for example, the graphical display 136 to use the affected limb and/or discourage use of the unaffected limb at block 208. The reminder message (visual, audible, and/or vibrotactile) can communicate the $\beta$, $\Psi$, and/or ratio of $\beta$ to $\Psi$. If $\beta$ is equal to or greater than $\Psi$, at block 210, no feedback (visual or tactile) can be provided. In some embodiments, the user can receive a reward message at block 210 when $\beta$ is equal to or greater than $\Psi$. The reward message can be displayed to the user on, for example, the graphical display 136 and/or can be communicated via audible and/or vibrotactile messages.

In some embodiments, body segment movement data can be transmitted and displayed to a third party (e.g., a clinician, coach, and/or trainer). The third party can provide feedback to the wearer of the sensor 110. The data can be transmitted to the third party via wireless networks and/or an internet interface. In some embodiments, the sensor 110 can be given to the third party for direct offloading of data (e.g., via USB or other means).

Computer System Embodiment

Figure 7:
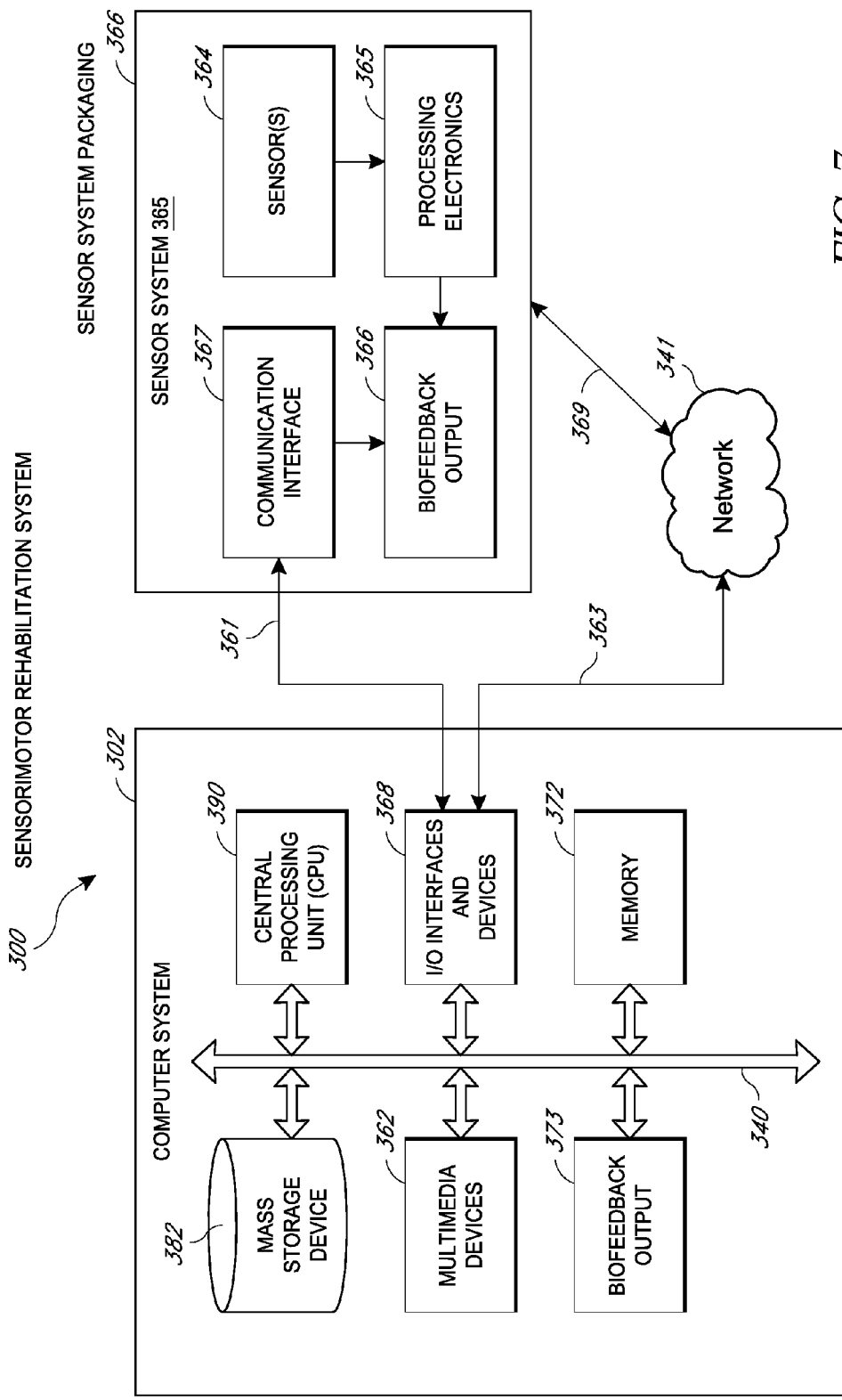
FIG. 7 is a block diagram illustrating an example embodiment of a sensorimotor rehabilitation system in accordance with some embodiments.

FIG. 7 is a block diagram illustrating an example embodiment of a sensorimotor rehabilitation system 300 (e.g., sensorimotor analysis and feedback system) in accordance with some embodiments. The system 300 can include a programmed computer system that comprises one or more computers or computing devices (e.g., smartphones or other mobile devices, laptop computers, application servers, database servers, workstations, storage servers, etc.) that execute code modules.

In some embodiments including the illustrated embodiment, the sensorimotor rehabilitation system 300 includes a computer system 302 and a sensor system 365 housed in a sensor system packaging 366. The packaging 366 can be any appropriate type of packaging and can be adapted to attach to the patient's shoulder, upper arm, elbow, forearm, wrist, hand, or fingers, or associated clothing, such as a sleeves, gloves, or the like. For instance, the packaging 366 can be similar to that shown with respect to the sensor 110 and/or the base 124 of FIGS. 3-4. The sensor system 365 can include, and in the illustrated embodiment does include, one or more body worn sensors 364, processing electronics 365, biofeedback output 366, and a communication interface 367.

The sensor(s) 364 can be any of the sensors described herein including inertial sensors such as accelerometers and/or gyroscopes, and can also include other types of sensors including magnetometers. Depending on the embodiment, combinations of any of the foregoing sensor types can be used.

The processing electronics 365 can generally be configured to process the data received from the sensors 364, and may include digital logic circuitry. For instance, the processing electronics 365 can be implemented using one or more microprocessors, microcontrollers, field-programmable gate arrays (FPGAs), combinations of the same or the like. In some cases the processing electronics 364 can also include appropriate analog circuitry, e.g., front-end circuitry including analog-to-digital converters and associated componentry for processing signals received from the sensors 364.

The processing electronics 365 can include a microprocessor executing firmware or other programmable instructions configured to implement an algorithm for determining one or more characteristics associated with body segment movement (e.g., upper limbs 112) of a person wearing the sensors 364 and/or to provide feedback information related to the body segment movement (e.g., feedback information related to one or more corrective actions for improving sensorimotor rehabilitation or performing exercises). The processing electronics 365 can be designed to determine any of the characteristics described herein (e.g., ratio of affected to unaffected limb use, quantity and/or type of movement, exercise performance, etc.) and/or provide information usable to generate any of the types of feedback described herein (e.g., visual, audible, tactile, etc.).

The biofeedback output 366 is in communication with the processing electronics 365 (and in some cases directly with the sensors 364), and can generally be configured to provide biofeedback to the user based on feedback information received from the processing electronics 365. For instance, the biofeedback output can comprise a liquid crystal or other type of display for providing graphical feedback, a touch-screen display, one or more light-emitting diodes or other visual indicators, a speaker for providing audible feedback, a vibration mechanism for providing tactile feedback, or any combination thereof. In some embodiments, the sensor system 365 does not include the biofeedback output 366, and instead communicates feedback information to the computer system 302 which in turn outputs the biofeedback to the user. In some embodiments, the computer system 302 and the sensor system 365 are both capable of providing biofeedback to the user.

The communication interface 367 can include a wireless transceiver or transmitter for delivering information to the computer system 302 over the communication link 361. The interface 367 can support any appropriate protocol (e.g., Bluetooth). In some cases, the sensor system 365 and the computer system 302 communicate over a wired link instead of a wireless link.

The computer system 302 can comprise one or more mobile devices or personal computers, such as one or more mobile devices or computers that are Windows, Macintosh, Android, iOS, or Linux/Unix compatible. In some embodiments, the computer system 302 comprises one or more servers, desktop computers, laptop computers, personal digital assistants, kiosks, or mobile devices (e.g., smartphones), for example. The exemplary computer system 302 includes a central processing unit ("CPU") 390, which may include one or more conventional microprocessors. The computer system 302 can further include memory 372, such as random access memory ("RAM") for temporary storage of information and a read only memory ("ROM") for permanent storage of information, and/or a mass storage device 382, such as a hard drive, diskette, solid-state drive, or optical media storage device. The mass storage device 382 may store data collected from a plurality of sensors or remotely collected sensor data, and/or calculated body segment parameter data from various trials. The components and modules of the computer system 302 can be connected using a bus system 340. In some embodiments, the bus system 340 is compatible with one or more of Peripheral Component Interconnect ("PCI"), Micro-channel, Small Computer System Interface ("SCSI"), Industrial Standard Architecture ("ISA") and Extended ISA ("EISA") architectures, for example. In some embodiments, the functionality provided for in the components and modules of the sensorimotor rehabilitation system 300 may be combined into fewer components and modules or further separated into additional components and modules.

The computer system 302 can be controlled and coordinated by operating system software, such as Windows Server, Linux Server, Windows XP, Windows Vista, Windows 7, Unix, Linux, SunOS, Solaris, Android, iOS, or other compatible server, desktop, or mobile operating systems. In Macintosh systems, the operating system may be any available operating system, such as MAC OS X. In other embodiments, the computer system 300 may be controlled by a proprietary operating system. Conventional operating systems control and schedule computer processes for execution, perform memory management, provide file system, networking, I/O services, and provide a user interface, such as a graphical user interface ("GUI"), among other things.

The computer system 302 may include one or more commonly available input/output (I/O) devices and interfaces 368, such as a keyboard, mouse, touchpad, and printer. The I/O devices may also include the one or more sensors 364 worn on a user's body, as described above. In some embodiments, these devices may be linked physically to the system 302, or may be linked wirelessly via interfaces such as Bluetooth.

The computer system 302 can also include a biofeedback output 373, which can be a separate from or form a part of the I/O devices and interfaces 368, and can include one or more display device, such as a monitor, that allows the visual presentation of data to a user (e.g., the visual feedback user interface described above for providing visual feedback relating to body segment movement and/or corrective actions for improving sensorimotor rehabilitation). More particularly, a display device provides for the presentation of GUIs, application software data, and multimedia presentations, for example. The biofeedback output 373 can include one or more speakers and/or tactile output devices (e.g., vibration mechanisms) for providing audible and tactile biofeedback, respectively, relating to body segment movement or corrective actions for improving sensorimotor rehabilitation.

The sensorimotor rehabilitation system 300 may also include one or more multimedia devices 362, video cards, graphics accelerators, and microphones, for example. In some embodiments, such as when the sensorimotor rehabilitation system 300 comprises a network server, for example, the computing system may not include any of the above-noted man-machine I/O devices.

In some embodiments, the I/O devices and interfaces 368 provide a communication interface to various external devices. For example, the sensorimotor rehabilitation system 300 can electronically couple to the network 341, which may comprise one or more of a LAN, WAN, or the Internet, for example, via a wired, wireless, or combination of wired and wireless, communication link 363. The network 341 can facilitate communications among various computing devices and/or other electronic devices via wired or wireless communication links. The sensorimotor rehabilitation system 300 may use network 341 to receive sensor data collected remotely and transmit such resulting data back to the user. For example, a user may wear sensors 110 during activities of daily living. The sensors 110 may be configured to transmit data (through a wired or wireless connection) to a mobile computing device (e.g., a smartphone, a laptop computer, a tablet, etc.). The mobile communication device may in turn transmit the collected sensor data via the network 341 to the sensorimotor rehabilitation system 300, which may, as described above, process the received data and provide feedback data back to the mobile computing device. The feedback data may then be used by the mobile computing device to display a visual feedback to the user (e.g., via a user interface described above). In this manner, the user can receive near-instantaneous feedback of body segment movement. As shown, the sensor system 365 can also be in communication with the network 341. For instance, the sensor system 365 and the computer system 302 in some embodiments are in communication with one another via a WAN, LAN or other network 341 via the link 369 instead of communicating via the link 361.

As illustrated, the functionality of the sensorimotor rehabilitation system 300 can be distributed between the computer system 302 and the sensor system 365. For instance, in some embodiments, the sensor system 365 generally obtains sensor data relating to a person's body segment movement, processes the sensor data to identify characteristics associated with the quantity or type of the body segment movement and/or generates information for providing feedback regarding the quantity or type of the body segment movement, such as feedback for improving sensorimotor rehabilitation. The computer system 302 receives the feedback information and outputs the information using the biofeedback output 373. One benefit of this configuration is that relatively less information may be sent between the sensor system 365 and the computer system 302 as compared to a situation where the computer system 302 processes the sensor data itself. For instance, the processing electronics 365 may generate relatively lightweight descriptors (e.g., 8-bit or 16-bit descriptors) or identifiers relating to certain identified body segment movement characteristics and/or types of biofeedback, which are forwarded to the computer system 302 via the communication interface 367.

The functionality of the sensorimotor rehabilitation system 300 can be distributed in other ways, depending on the embodiment. For example, in some cases, the processing electronics 365 is not included, or performs minimal processing on the data obtained from the sensor 364. The sensor data is forwarded to the computer system 302 which implements the algorithm for analyzing body segment movement, generating feedback information, and the like. In other cases, such as where the sensor system 365 includes the biofeedback output 366, the entire sensorimotor rehabilitation system 300 resides in the sensor system packaging 366, and a separate computer system 302 is not used.

In addition to the devices that are illustrated in, for example, FIGS. 2-5, the sensorimotor rehabilitation system 300 may communicate with other data sources or other computing devices. For example, collected data may be stored in a local or remote database by the sensorimotor rehabilitation system 300, so that a user's performance can be tracked over time.

The sensorimotor rehabilitation system 300 may also include one or more software modules to process perform the functionalities discussed herein, for example, the methods and processes in FIGS. 1 and 6. The software module may be stored in mass storage 382 and/or memory 372, and implemented as one or more modules, which may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Alternately, the software module may be implemented as separate devices, such as computer servers. In alternate embodiments, the postural and balance evaluation system can be implemented by multiple physical computers that are interconnected, with different functions or tasks optionally handled by different machines.

In general, the word "module," as used herein, refers to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

Long-Term Monitoring and Telehealth Infrastructures

In some embodiments, the sensorimotor rehabilitation system can provide a log of usage (e.g., body movement) of the affected and the unaffected limbs in, for example, a log mode of operation. This information (e.g., usage log, usage indication, usage number, and/or usage score) can be relayed to the patient and/or to a caregiver so that they are aware of their relative usage of each limb over an extended period of time (e.g., one day, multiple days, and/or one week) and can thus use this information to help achieve targeted limb usage goals (e.g., use the affected limb 75% of the time) as discussed herein. In some embodiments, the usage log for each limb can include a history of specific movements (e.g., reaching, writing, eating, or performing prescribed rehabilitative exercises and/or the like as discussed herein). In some embodiments, the usage score (e.g., performance score) can indicate a level of compliance of the patient with the prescribed, predetermined, and/or desired sensorimotor rehabilitation therapy such as, for example, performance of the rehabilitation exercises (e.g., percent of prescribed rehabilitation exercises performed) and/or quantity of body movement during ADLs (e.g., ratio of affected limb movement to unaffected limb movement).

In some embodiments, the usage log can be displayed on the sensors 110 as discussed herein (e.g., a graphical display 136 on each sensor 110 indicates the accumulation of movements for the associated limb, such as the limb that a particular sensor 110 is being worn on). The usage log can be periodically reset (e.g., each day or each week). In some embodiments, the usage log can be provided to the user via an external electronic device, such as a personal computer, mobile phone, tablet computer, or other electronic device as discussed herein. In some embodiments, data can be transmitted and displayed to a third party (e.g., a therapist) and then the third party can provide feedback to the wearer. The data corresponding to the usage log can be transmitted to the third party via wireless networks and/or an internet interface, and/or the sensor can be given to the third party for direct offloading of data (e.g., via USB or other means) as discussed herein.

FIG. 8 illustrates an example embodiment of a sensorimotor rehabilitation system 300 with, for example, a telehealth infrastructure. The sensorimotor rehabilitation system 300 can have a sensor system package(s) 366 (e.g., sensor(s) 110 with sensor system(s) 365), link 361, link 363, link 369, network 341, and/or computer system 302 as discussed herein, and in particular, in reference to FIG. 7. One or more of the link 361, link 363, link 369, network 341, and/or computer system 302, including any of the components discussed in reference to FIG. 7, can form the telehealth infrastructure of the sensorimotor rehabilitation system 300. The telehealth infrastructure can be encrypted with, for example, industry standard and HIPPA compliant encryption protocols to protect security and privacy of patients. The telehealth infrastructure can be scalable (e.g., multiple sensors 110, computer systems 302, and/or servers 341). The server(s) 341 can be hosted by secure and reliable HIPAA compliant cloud computing services, such as Amazon Web Services, Microsoft Azure, and/or Google Computing Cloud. In some embodiments, the sensorimotor rehabilitation system 300 does not have a telehealth infrastructure or one of the components of the telehealth infrastructure, for example, where movement data may be logged by the sensor system 365 and downloaded during clinical visits.

As illustrated in FIG. 8, the sensorimotor rehabilitation system 300 can have a base station 310. The base station 310 can plug into a wall outlet in the patient's home and automatically transmit data to a secure website via links 363, 369 and network 341 (e.g., server). The secure website can be viewed via the computer system 302 where therapists can, for example, view movement data, adjust exercise plans, and/or set patient specific goals for the use of the affected limb. Therapists can timely intervene if patients are not complying with prescribed at home exercises and/or are not attempting to use their affected limb frequently enough during regular activities. In some embodiments, patients can access the same secure website or modified website (e.g., patient is not able to adjust patient specific goals). For some patients, seeing movement activities logged on a website and rehabilitation progress can be motivating to continue with sensorimotor therapy.

The base station 310 can receive daily (or other periods as discussed herein) movement summaries from the sensor system 365. The base station 310 can upload the data via WiFi or LAN (e.g., link 369) to a HIPAA compliant server 341 (e.g., a cloud based system), where a physician and/or patient can securely access the website to view movement data, adjust exercise plans, and/or set patient specific goals for the use of the affected limb. For example, at the start of sensorimotor rehabilitation therapy, the patient can be encouraged to use the affected limb 90% of the time to promote motor recovery (traditional CIMT consists of constraining the affected limb for up to 90% of waking hours). Over time as sensorimotor rehabilitation therapy progresses, the target for daily use of the affected limb can be changed or adjusted by the therapist to reflect the recovery process. Remote adjustment of patient specific goals can extend the treatment period via prolonged biofeedback (e.g., for several months) after, for example, the initial prescribed period of extremely limited use of the unaffected limb (e.g., 2 weeks). Remote adjustment of patient specific goals can reduce frequency of clinical visits throughout sensorimotor rehabilitation therapy.

The base station 310 can be a maintenance free or substantially maintenance free device (from the patient's perspective) that can placed in a home of the patient. The base station 310 can receive movement data via, for example, Bluetooth low energy protocol (BLE) from a sensor system 365 (e.g., a sensor 110 having a watch form). In some embodiments, the link 360 can be an extended wireless protocol, such as for example, Wi-Fi. The base station 310 can transfer the data over an Internet connection via link 369 as discussed herein to a remote server 341. The transfer to and/or from the base station 310 can be done at any desired or predetermined frequency, such as for example, hourly, 4 times a day, 2 times a day, daily, biweekly, weekly, etc.

The base station 310 can have a computer system 302 as discussed herein. In some embodiments, the base station can have a display or connect to a display to show movement data and related information as discussed herein. In some embodiments, the patient 310 does not interact with the base station 310. The base station 310 can act a standalone device for transferring body movement data as discussed herein without patient interaction. The base station 310 can be powered through a standard electrical outlet and/or operate on battery power for portability. The base station 310 can access the Internet through wired-Ethernet, Wi-Fi, 3G/4G mobile Internet services, and/or the like.

In some embodiments, the base station 310 can have a plug computer platform with, for example, a 1.2 GHz ARM-family CPU, 512 MB memory capacity, and expandable flash storage. The base station 310 can maintain reliable communication channels with the sensor system 366 and server 341 as discussed herein. For example, the base station 310 can have a Debian-based Embedded Linux operating system built for ARM-based RISC. A status report client can allow the base station 310 to collect maintenance data from the sensor system 365 and pass that information on the server 341 for review by, for example, a clinician. A local configuration module can allow the server 341 to remotely reconfigure the base station 310 and the sensor system 365 for maintenance purposes, such as firmware upgrades, as well as to change prescribed exercise routines and adjust biofeedback rules.

As illustrated in FIG. 8, when the sensorimotor rehabilitation system 300 is utilized with one or more sensor system packages 366 (e.g., one or more sensor systems 365), the sensor systems 365 can pair and communicate via any suitable wired and/or wireless protocol between the sensor system systems 365 and/or base station 310. The wireless communication protocol can be BLE as discussed herein to, for example, extend the battery life of the sensor system 365. In some embodiments, the wireless communication protocol can be Wi-Fi to, for example, extend the range of communication between the base station 310 and at least one of the sensor systems 365 worn by the patient.

The following is a list of example embodiments. The features recited in the below list of example embodiments can be combined with additional features disclosed herein. Furthermore, additional inventive combinations of features are disclosed herein, which are not specifically recited in the below list of example embodiments and which do not include the same features as the specific embodiments listed below. For sake of brevity, the below list of example embodiments does not identify every inventive aspect of this disclosure. The below list of example embodiments are not intended to identify key features or essential features of any subject matter described herein.

1. A method for sensorimotor rehabilitation, the method comprising:
  receiving one or more signals generated by at least one inertial sensor supported at a position on an affected upper limb of a person;
  with processing electronics comprising digital logic circuitry, processing sensor data derived from the one or more signals to identify a characteristic associated with at least one of a quantity of upper limb movement of the person or a type of upper limb movement of the person; and based at least in part on the identified characteristic, generating information usable to present feedback usable in sensorimotor rehabilitation of the upper limb.

2. The method of Embodiment 1, wherein the feedback is indicative of a corrective action for improving sensorimotor rehabilitation.

3. The method of Embodiment 1, wherein the inertial sensor is attached to a wrist of the affected upper limb of the person.

4. The method of Embodiment 1, wherein the inertial sensor is attached to a finger of the person, a hand of the person, a wrist of the person, a forearm of the person, or an upper arm of the person 5. The method of Embodiment 1, wherein the one or more signals are generated by at least two inertial sensors, wherein a first inertial sensor of the at least two inertial sensors is supported at a first position on the affected upper limb of the person, and a second inertial sensor of the at least two inertial sensors is supported at a second position on an unaffected upper limb of the person, and the affected limb exhibits more limited motor control than the unaffected limb due to nervous system damage of the person.

6. The method of Embodiment 5, wherein the characteristic is associated with the quantity of upper limb movement of the person, and wherein the characteristic comprises a ratio of affected upper limb movement to unaffected upper limb movement.

7. The method of Embodiment 6, wherein the ratio of affected upper limb movement to unaffected upper limb movement is associated with a quantity of one or more types or groups of upper limb movements.

8. The method of Embodiment 6, wherein a packaging containing at least one of the at least two inertial sensors comprises a graphical display configured to display the ratio of affected upper limb movement to unaffected upper limb movement.

9. The method of Embodiment 6, further comprising displaying a reward message in association with the first sensor when the ratio of affected upper limb movement to unaffected upper limb movement is above a predetermined ratio.

10. The method of Embodiment 6, further comprising vibrating a packaging that supports the second sensor to generate a vibrotactile message when the ratio of affected upper limb movement to unaffected upper limb movement is below a predetermined ratio to discourage use of the unaffected upper limb.

11. The method of Embodiment 6, further comprising vibrating a packaging that supports at least one of the at least two inertial sensors to generate a vibrotactile message when the ratio of affected upper limb movement to unaffected upper limb movement is below a predetermined ratio to discourage use of the unaffected upper limb.

12. The method of Embodiment 6, wherein a packaging containing the second sensor does not comprise a graphical display.

13. The method of Embodiment 6, wherein at least one of the at least two inertial sensors is configured to provide at least one of auditory positive feedback, visual positive feedback, or tactile positive feedback to the user when the ratio of affected upper limb movement to unaffected upper limb movement is equal to or greater than a predetermined ratio or configured to provide at least one of auditory negative feedback, visual negative feedback, or tactile negative feedback to the user when the ratio of affected upper limb movement to unaffected upper limb movement is less than a predetermined ratio.

14. The method of Embodiment 1, wherein the characteristic is associated with the quantity of upper limb movement of the person, and wherein the quantity of upper limb movement of the person is associated with a quantity of one or more types or groups of upper limb movements.

15. The method of Embodiment 14, further comprising, with the processing electronics, determining the one or more types or groups of upper limb movements by at least one of:
estimating upper limb kinematics from measured the sensor data and identifying the one or more types or groups based on the estimated upper limb kinematics; or
applying classification rules to the measured the sensor data, the classification rules based at least in part on artificial intelligence classification methods or statistical classification methods.

16. The method of Embodiment 14, further comprising displaying a sequence of images depicting a sensorimotor rehabilitation exercise to be performed by the person, the sensorimotor rehabilitation exercise comprising the one or more types or groups of upper limb movements.

17. The method of Embodiment 16, wherein the sequence of images change to reflect changes in upper limb movement that are identified by the processing during the sensorimotor rehabilitation exercise.

18. The method of Embodiment 1, wherein the characteristic is associated with the type of upper limb movement of the person which tracks sensorimotor rehabilitation progress.

19. The method of Embodiment 18, wherein the characteristic comprises a rehabilitation progress score indicating sensorimotor rehabilitation progress during a sensorimotor rehabilitation exercise.

20. The method of Embodiment 1, further comprising wirelessly transmitting to a separate computer system the information usable to present the feedback.

21. The method of Embodiment 1, wherein the one or more signals are generated by at least two inertial sensors, and wherein the identified characteristic comprises a ratio of upper limb movements of the person.

22. The method of Embodiment 1, wherein the generating feedback information comprises generating the feedback information for real time presentation.

23. The method of Embodiment 1, wherein the generating feedback information further comprises generating information for use in generating a graphical depiction of a predetermined upper limb movement which changes to reflect changes in upper limb movement that are identified by the processing, the graphical depiction associated with a sensorimotor rehabilitation exercise.

24. The method of Embodiment 1, wherein the generating feedback information comprises generating audible feedback indicative of one or more of the identified characteristic and a suggested corrective action.

25. The method of Embodiment 1, wherein the generating feedback information comprises generating visual feedback indicative of one or more of the identified characteristic and a suggested corrective action.

26. The method of Embodiment 1, wherein the generating feedback information comprises electronically storing the feedback information for later access of the feedback information.

27. The method of Embodiment 1, further comprising logging the information over a predetermined period of time for later access of the feedback information, wherein the feedback comprises a usage log of the affected upper limb over the predetermined period of time based at least in part on the identified characteristic.

28. The method of Embodiment 27, further comprising determining a performance score based on the logged information indicating a level of compliance of the patient with sensorimotor rehabilitation therapy.

29. The method of Embodiment 1, wherein the generating feedback information comprises generating tactile or vibrotactile feedback indicative of one or more of the identified characteristic and a suggested corrective action.

30. The method of Embodiment 1, wherein the method exclusively utilizes sensors supported by the person's body.

31. The method of Embodiment 1, wherein the method does not involve constraining upper limb movement of the person.

32. The method of Embodiment 1, wherein the at least one inertial sensor comprises an accelerometer.

33. The method of Embodiment 1, wherein the at least one inertial sensor comprises a gyroscope.

34. A sensorimotor rehabilitation system, the system comprising:
at least one inertial sensor configured to generate one or more signals; and processing electronics in communication with the at least one inertial sensor and comprising digital logic circuitry, the processing electronics configured to:

process sensor data derived from the one or more signals according to a sensorimotor analysis algorithm, wherein the sensor data is collected while the inertial sensor is supported on a finger of a person, a hand of the person, a wrist of the person, a forearm of the person, or an upper arm of the person;

based at least in part on the results of the processing of the sensor data, identify a characteristic associated with at least one of the quantity of limb movement of the person or the type of limb movement of the person; and based at least in part on the identified characteristic, generate information usable to present feedback.

35. The system of Embodiment 34, wherein the inertial sensor and the processing electronics are housed together in a packaging.

36. The system of Embodiment 35, wherein the packaging comprises an attachment mechanism configured to allow the packaging to be attached to one or more of the wrist, the forearm, and the upper arm of the person.

37. The system of Embodiment 34, wherein the inertial sensor is housed in a packaging comprising an engagement mechanism configured to mate with a mounting unit to releasably secure the packaging to a sensor mount unit attached to the person or to an article of the person's clothing.

38. The system of Embodiment 37, wherein the sensor mount unit includes one or more holes each dimensioned to pass a band therethrough, thereby allowing the mount unit to be fastened around a limb of the person.

39. The system of Embodiment 34, further comprising a wireless transmitter configured to send to a separate computer system the information usable to present the feedback.

40. The system of Embodiment 34, wherein at least a portion of the processing electronics resides in a computer system that is separate from a housing that contains the inertial sensor.

41. The system of Embodiment 34, wherein the processing electronics are configured to generate the feedback information for real time presentation.

42. The system of Embodiment 34, wherein the feedback information is usable to generate audible feedback indicative of one or more of the identified characteristic and a suggested corrective action.

43. The system of Embodiment 34, wherein the feedback information is usable to generate visual feedback indicative of one or more of the identified characteristic and a suggested corrective action.

44. The system of Embodiment 34, wherein the processing electronics are further configured to electronically store the feedback information for later access of the feedback information.

45. The system of Embodiment 34, wherein the processing electronics are further configured to electronically store the feedback information over a predetermined period of time for later access of the feedback information, wherein the feedback information comprises a usage indication of limb movement over the predetermined period of time based at least in part on the identified characteristic.

46. The system of Embodiment 34, wherein the processing electronics are further configured to generate tactile or vibrotactile feedback information indicative of one or more of the identified characteristic and a suggested corrective action.

47. The system of Embodiment 34, wherein the feedback is indicative of a corrective action for improving sensorimotor rehabilitation.

48. The system of Embodiment 34, wherein the inertial sensor is attached to the wrist of an upper limb of the person.

49. The system of Embodiment 34, wherein the one or more signals are generated by at least two inertial sensors, wherein a first inertial sensor of the at least two inertial sensors is supported at a first position on the affected upper limb of the person, and a second inertial sensor of the at least two inertial sensors is supported at a second position on an unaffected upper limb of the person, and the affected limb exhibits more limited motor control than the unaffected limb due to nervous system damage of the person.

50. The system of Embodiment 49, wherein the characteristic is associated with the quantity of upper limb movement of the person, and wherein the characteristic comprises a ratio of affected upper limb movement to unaffected upper limb movement.

51. The system of Embodiment 50, wherein the ratio of affected upper limb movement to unaffected upper limb movement is associated with a quantity of one or more types or groups of upper limb movements.

52. The system of Embodiment 50, wherein a packaging containing at least one of the at least two inertial sensors comprises a graphical display configured to display the ratio of affected upper limb movement to unaffected upper limb movement.

53. The system of Embodiment 50, wherein a packaging containing the first sensor comprises a graphical display configured to display the ratio of affected upper limb movement to unaffected upper limb movement.

54. The system of Embodiment 50, wherein a packaging containing at least one of the at least two inertial sensors comprises a graphical display configured to display a reward message when the ratio of affected upper limb movement to unaffected upper limb movement is above a predetermined ratio.

55. The system of Embodiment 50, wherein a packaging containing the first sensor comprises a graphical display configured to display a reward message when the ratio of affected upper limb movement to unaffected upper limb movement is above a predetermined ratio.

56. The system of Embodiment 50, wherein at least one of the at least two inertial sensors is configured to provide at least one of auditory positive feedback, visual positive feedback, or tactile positive feedback to the user when the ratio of affected upper limb movement to unaffected upper limb movement is equal to or greater than a predetermined ratio or configured to provide at least one of auditory negative feedback, visual negative feedback, or tactile negative feedback to the user when the ratio of affected upper limb movement to unaffected upper limb movement is less than a predetermined ratio.

57. The system of Embodiment 49, wherein a packaging containing at least one of the at least two inertial sensors comprises a vibration mechanism configured to generate a vibrotactile message when the ratio of affected upper limb movement to unaffected upper limb movement is below a predetermined ratio to discourage use of the unaffected upper limb.

58. The system of Embodiment 49, wherein a packaging containing the second sensor comprises a vibration mechanism configured to generate a vibrotactile message when the ratio of affected upper limb movement to unaffected upper limb movement is below a predetermined ratio to discourage use of the unaffected upper limb.

59. The system of Embodiment 49, wherein a packaging containing the second sensor does not comprise a graphical display.

60. The system of Embodiment 34, wherein the characteristic is associated with the type of limb movement of the person which tracks sensorimotor rehabilitation progress.

61. The system of Embodiment 34, wherein the characteristic comprises a rehabilitation progress score indicating sensorimotor rehabilitation.

62. The system of Embodiment 34, wherein the characteristic is associated with the quantity of upper limb movement of the person, and wherein the quantity of upper limb movement of the person is associated with a quantity of one or more types or groups of upper limb movements.

63. The system of Embodiment 62, wherein the processing electronics, are further configured to determine the one or more types or groups of upper limb movements by at least one of:
estimating upper limb kinematics from measured the sensor data and identifying the one or more types or groups based on the estimated upper limb kinematics; or
applying classification rules to the measured the sensor data, the classification rules based at least in part on artificial intelligence classification methods or statistical classification methods.

64. The system of Embodiment 62, wherein a packaging containing the first sensor comprises a graphical display configured to display a sequence of images depicting a sensorimotor rehabilitation exercise to be performed by the person, the sensorimotor rehabilitation exercise comprising the one or more types or groups of upper limb movements.

65. The system of Embodiment 64, wherein the sequence of images changes to reflect changes in upper limb movement that are identified by the processing during the sensorimotor rehabilitation exercise.

66. The system of Embodiment 34, wherein the one or more signals are generated by at least two inertial sensors, and wherein the identified characteristic comprises a ratio of upper limb movements of the person.

67. The system of Embodiment 34, wherein the processing electronics generates the feedback information by generating information for use in generating a graphical depiction of a predetermined limb movement which changes to reflect changes in limb movement that are identified by the processing, the graphical depiction associated with a sensorimotor rehabilitation exercise.

68. The system of Embodiment 34, wherein the system exclusively utilizes sensors supported by the person's body.

69. The system of Embodiment 34, wherein the at least one inertial sensor comprises an accelerometer.

70. The system of Embodiment 34, wherein the at least one inertial sensor comprises a gyroscope.

71. The system of Embodiment 34, wherein the processing electronics are further configured to log the information over a predetermined period of time for later access of the feedback information, wherein the feedback comprises a usage log of the affected upper limb over the predetermined period of time based at least in part on the identified characteristic.

72. The system of Embodiment 71, wherein the processing electronics are further configured to determine a performance score based on the logged information indicating a level of compliance of the patient with sensorimotor rehabilitation therapy.

73. Non-transitory computer storage that stores executable code that directs computer hardware to at least:
process sensor data derived from one or more signals generated by at least one inertial sensor according to a sensorimotor analysis algorithm, wherein the algorithm is designed such that processing the sensor data according to the algorithm using sensor data obtained when the sensor is supported a finger of a person, a hand of the person, a wrist of the person, a forearm of the person, or an upper arm of the person;
based at least in part on results of the processing of the sensor data, identify a characteristic associated with at least one of the quantity of limb movement of the person or the type of limb movement of the person; and
based on the identified characteristic, generating information usable to present feedback.

74. A system comprising:
computer hardware configured to:
process data relating to motor function of a person, the data derived from sensor information generated by application of an algorithm to the sensor information, the sensor information collected from at least one inertial sensor while the sensor is supported by a finger, hand, wrist, forearm, or upper arm of the person; and
in response to the processing, generate feedback information usable to output feedback relating to at least one of a quantity of limb movement of the person or a type of limb movement of the person; and
a feedback unit configured to output the feedback based on the feedback information.

75. The system of Embodiment 74, wherein the feedback is a vibrotactile message and the feedback unit comprises a vibrotacitle motor configured to output the vibrotactile message 76. The system of Embodiment 74, wherein the feedback is a graphical depiction and the feedback unit comprises an electronic display screen configured to display the graphical depiction.

77. The system of Embodiment 74, wherein the feedback is audible feedback and the feedback unit comprises a speaker.

78. The system of Embodiment 74, wherein the data relating to the motor function of the person comprises one or more descriptors each representative of a particular characteristic associated with motor function.

79. The system of Embodiment 74, wherein the system is a computer system contained in a separate housing than the at least one inertial sensor.

80. Non-transitory computer storage that stores executable code that directs computer hardware to at least:
process data relating to at least one of a quantity of limb movement of a person or a type of limb movement of the person, the data derived from body worn sensor information generated by application of an algorithm to the sensor information, the sensor information collected from at least one inertial sensor while the sensor is supported by a finger, hand, wrist, forearm, or upper arm of the person; and
in response to the processing, present biofeedback relating to at least one of the quantity of limb movement of the person or the type of limb movement of the person.

81. A method of analyzing motor function, comprising:
receiving one or more signals generated by at least one inertial sensor supported at a position on an upper limb of a person; and
with processing electronics, processing sensor data derived from the one or more signals to identify a characteristic associated with at least one of a quantity of upper limb movement of the person or a type of upper limb movement of the person.

82. A method of analyzing motor function of a person, the method comprising:

receiving one or more signals generated by at least one inertial sensor supported at a position on an upper limb of a person; and with processing electronics, processing sensor data derived from the one or more signals to identify a characteristic associated with the motor function of the person;

compare the characteristic to desired motor function; and based on the comparison, providing information usable to present feedback relating to a corrective action for improving motor function of the person.

TERMINOLOGY

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially.

Systems and modules described herein may comprise software, firmware, hardware, or any combination(s) of software, firmware, or hardware suitable for the purposes described herein. Software and other modules may reside on servers, workstations, personal computers, computerized tablets, PDAs, and other devices suitable for the purposes described herein. Software and other modules may be accessible via local memory, via a network, via a browser, or via other means suitable for the purposes described herein. Data structures described herein may comprise computer files, variables, programming arrays, programming structures, or any electronic information storage schemes or methods, or any combinations thereof, suitable for the purposes described herein. User interface elements described herein may comprise elements from graphical user interfaces, command line interfaces, and other suitable interfaces.

Further, the processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems. Likewise, the data repositories shown can represent physical and/or logical data storage, including, for example, storage area networks or other distributed storage systems. Moreover, in some embodiments the connections between the components shown represent possible paths of data flow, rather than actual connections between hardware. While some examples of possible connections are shown, any of the subset of the components shown can communicate with any other subset of components in various implementations.

Embodiments are also described above with reference to flow chart illustrations and/or block diagrams of methods, apparatus (systems) and computer program products. Each block of the flow chart illustrations and/or block diagrams, and combinations of blocks in the flow chart illustrations and/or block diagrams, may be implemented by computer program instructions. Such instructions may be provided to a processor of a general purpose computer, special purpose computer, or other programmable data processing apparatus to produce a machine, such that the instructions, which execute via the processor of the computer or other programmable data processing apparatus, create means for implementing the acts specified in the flow chart and/or block diagram block or blocks.

These computer program instructions may also be stored in a computer-readable memory that can direct a computer or other programmable data processing apparatus to operate in a particular manner, such that the instructions stored in the computer-readable memory produce an article of manufacture including instruction means which implement the acts specified in the flow chart and/or block diagram block or blocks. The computer program instructions may also be loaded onto a computer or other programmable data processing apparatus to cause a series of operations to be performed on the computer or other programmable apparatus to produce a computer implemented process such that the instructions which execute on the computer or other programmable apparatus provide steps for implementing the acts specified in the flow chart and/or block diagram block or blocks.

While certain embodiments have been described, these embodiments have been presented by way of example only, and are not intended to limit the scope of the disclosure. Indeed, the novel methods and systems described herein may be embodied in a variety of other forms; furthermore, various omissions, substitutions and changes in the form of the described methods and systems may be made without departing from the spirit of the disclosure. The accompanying claims and their equivalents are intended to cover such forms or modifications as would fall within the scope and spirit of the disclosure.

The terms affected limb and unaffected limb are used to refer to the upper limbs of an individual who has an upper extremity motor impairment. For individuals with a symmetric impairment, that is the right and left upper limbs have a relatively equal level of impairment, then both limbs would be termed affected limbs. For individuals with an asymmetric motor impairment, that is one limb has a more significant motor impairment than the other limb, then the more impaired limb is termed 'affected' and the less impaired limb is termed 'unaffected' even if both limbs have some level of impairment.

What is claimed is:

1. A method for sensorimotor rehabilitation, the method comprising:
   receiving one or more signals generated by at least one body-worn inertial sensor supported by an affected upper limb of a person to automatically detect movement of the affected limb during activities of daily living;
   with processing electronics comprising digital logic circuitry, processing sensor data derived from the one or more signals to identify a characteristic associated with at least one of a quantity of upper limb movement of the person during the activities of daily living or a type of upper limb movement of the person during the activities of daily living; and
   based at least in part on the identified characteristic, electronically generating information usable to present feedback usable in sensorimotor rehabilitation of the affected upper limb.

2. The method of claim 1, wherein the feedback is indicative of a corrective action for improving sensorimotor rehabilitation.

3. The method of claim 1, wherein the body-worn inertial sensor is attached to a wrist of the affected upper limb of the person.

4. The method of claim 1, wherein the one or more signals are generated by at least two body-worn inertial sensors, wherein a first body-worn inertial sensor of the at least two body-worn inertial sensors is supported by the affected upper limb of the person, and a second body-worn inertial sensor of the at least two body-worn inertial sensors is supported by an unaffected upper limb of the person, and the affected limb exhibits more limited motor control than the unaffected limb due to nervous system damage of the person.

5. The method of claim 4, wherein the characteristic is associated with the quantity of upper limb movement of the person, and wherein the characteristic comprises a ratio of affected upper limb movement to unaffected upper limb movement.

6. The method of claim 5, wherein the ratio of affected upper limb movement to unaffected upper limb movement is associated with a quantity of one or more types or groups of upper limb movements.

7. The method of claim 5, wherein a packaging containing at least one of the at least two body-worn inertial sensors comprises a graphical display configured to display the ratio of affected upper limb movement to unaffected upper limb movement.

8. The method of claim 5, wherein at least one of the at least two body-worn inertial sensors is configured to provide at least one of auditory positive feedback, visual positive feedback, or tactile positive feedback to a user when the ratio of affected upper limb movement to unaffected upper limb movement is equal to or greater than a predetermined ratio or configured to provide at least one of auditory negative feedback, visual negative feedback, or tactile negative feedback to the user when the ratio of affected upper limb movement to unaffected upper limb movement is less than the predetermined ratio.

9. The method of claim 5, wherein the ratio corresponds to a quantity of movement of the affected limb relative to a quantity of the unaffected limb, wherein the quantity of movement of the affected limb and the quantity of the unaffected limb are different.

10. The method of claim 1, wherein the characteristic is associated with the quantity of upper limb movement of the person, and wherein the quantity of upper limb movement of the person is associated with a quantity of one or more types or groups of upper limb movements.

11. The method of claim 10, further comprising, with the processing electronics, determining the one or more types or groups of upper limb movements by at least one of:
   estimating upper limb kinematics from measured the sensor data and identifying the one or more types or groups based on the estimated upper limb kinematics; or
   applying classification rules to the measured the sensor data, the classification rules based at least in part on artificial intelligence classification methods or statistical classification methods.

12. The method of claim 10, further comprising displaying a sequence of images depicting a sensorimotor rehabilitation exercise to be performed by the person, the sensorimotor rehabilitation exercise comprising the one or more types or groups of upper limb movements.

13. The method of claim 12, wherein the sequence of images change to reflect changes in upper limb movement that are identified by the processing during the sensorimotor rehabilitation exercise.

14. The method of claim 1, further comprising wirelessly transmitting to a separate computer system the information usable to present the feedback.

15. The method of claim 1, further comprising logging the information over a predetermined period of time for later access of the feedback information, wherein the feedback comprises a usage log of the affected upper limb over the predetermined period of time based at least in part on the identified characteristic.

16. The method of claim 15, further comprising determining a performance score based on the logged information indicating a level of compliance of a patient with sensorimotor rehabilitation therapy.

17. The method of claim 1, wherein the affected upper limb is able to be moved by the person independently relative to movement of an unaffected upper limb of the person.

18. A sensorimotor rehabilitation system, the system comprising:
   at least one body-worn inertial sensor configured to generate one or more signals; and
   processing electronics in communication with the at least one body-worn inertial sensor and comprising digital logic circuitry, the processing electronics configured to:
      process sensor data derived from the one or more signals according to a sensorimotor analysis algorithm, wherein the sensor data is collected while the body-worn inertial sensor is supported by a finger of a person, a hand of the person, a wrist of the person, a forearm of the person, or an upper arm of the person;
      based at least in part on results of the processing of the sensor data, identify a characteristic associated with at least one of a quantity of limb movement of the person during activities of daily living or a type of limb movement of the person during the activities of daily living; and
      based at least in part on the identified characteristic, generate information usable to present feedback.

19. The system of claim 18, wherein the one or more signals are generated by at least two body-worn inertial sensors, wherein a first body-worn inertial sensor of the at least two body-worn inertial sensors is supported by an affected upper limb of the person, and a second body-worn inertial sensor of the at least two body-worn inertial sensors is supported by an unaffected upper limb of the person, and the affected limb exhibits more limited motor control than the unaffected limb due to nervous system damage of the person.

20. The system of claim 19, wherein the characteristic is associated with the quantity of upper limb movement of the person, and wherein the characteristic comprises a ratio of affected upper limb movement to unaffected upper limb movement.

21. The system of claim 20, wherein the ratio corresponds to a quantity of movement of the affected limb relative to a quantity of the unaffected limb, wherein the quantity of movement of the affected limb and the quantity of the unaffected limb are different.

22. The system of claim 18, further comprising a wireless transmitter configured to send to a separate computer system the information usable to present the feedback.

23. The system of claim 18, wherein the feedback information is usable to generate visual feedback indicative of one or more of the identified characteristic and a suggested corrective action.

24. The system of claim 18, wherein the processing electronics are further configured to electronically store the feedback information over a predetermined period of time for later access of the feedback information, wherein the feedback information comprises a usage indication of limb movement over the predetermined period of time based at least in part on the identified characteristic.

25. Non-transitory computer storage that stores executable code that directs computer hardware to at least:
  process sensor data derived from one or more signals generated by at least one body-worn inertial sensor according to a sensorimotor analysis algorithm, the sensor data obtained when the body-worn inertial sensor is supported by a finger of a person, a hand of the person, a wrist of the person, a forearm of the person, or an upper arm of the person;
  based at least in part on results of the processing of the sensor data, identify a characteristic associated with at least one of a quantity of limb movement of the person during activities of daily living or a type of limb movement of the person during the activities of daily living; and
  based on the identified characteristic, generating information usable to present feedback.

* * * * *